(12) United States Patent
Kodet et al.

(10) Patent No.: US 9,428,493 B2
(45) Date of Patent: Aug. 30, 2016

(54) SCHWEINFURTHIN ANALOGUES

(71) Applicant: University of Iowa Research Foundation, Iowa City, IA (US)

(72) Inventors: John Kodet, Iowa City, IA (US); Jeffrey D. Neighbors, Iowa City, IA (US); David F. Wiemer, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/388,202

(22) PCT Filed: Mar. 25, 2013

(86) PCT No.: PCT/US2013/033722
§ 371 (c)(1),
(2) Date: Sep. 25, 2014

(87) PCT Pub. No.: WO2013/148584
PCT Pub. Date: Oct. 3, 2013

(65) Prior Publication Data
US 2015/0045404 A1   Feb. 12, 2015

Related U.S. Application Data

(60) Provisional application No. 61/615,725, filed on Mar. 26, 2012.

(51) Int. Cl.
C07D 405/06 (2006.01)
C07D 405/14 (2006.01)

(52) U.S. Cl.
CPC ........... *C07D 405/06* (2013.01); *C07D 405/14* (2013.01)

(58) Field of Classification Search
CPC .................................................. C07D 407/06
See application file for complete search history.

(56) References Cited

U.S. PATENT DOCUMENTS

| | | | |
|---|---|---|---|
| 7,358,377 B2 | 4/2008 | Wiemer et al. | |
| 7,902,228 B2 | 3/2011 | Wiemer et al. | |
| 8,637,685 B2 | 1/2014 | Wiemer et al. | |
| 2008/0015232 A1 | 1/2008 | Wiemer et al. | |
| 2011/0319481 A1 | 12/2011 | Wiemer et al. | |

FOREIGN PATENT DOCUMENTS

| | | |
|---|---|---|
| WO | 2005092878 A2 | 10/2005 |
| WO | 2009158516 A1 | 12/2009 |
| WO | 2010127235 A1 | 11/2010 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wikilCancer.*
Beutler et al., "Cytotoxic Geranyl Stilbenes from Macaranga schweinfurthii", J. Nat. Prod., 61, 1509-1512 (1998).
Beutler et al., "Schweinfurthin D, A Cytotoxic Stilbene from Macaranga Schweinfurthii", Natural Product Letters, vol. 14(5), 399-404 (2000).
Beutler et al., "The Schweinfurthins: Issues in Development of a Plant-Derived Anticancer Lead", Medicinal and Aromatic Plants, edited by R. J. Bogers, Springer, 301-309 (2006).
Dermer, "Another Anniversary for the War on Cancer", BioTechnology, vol. 12, 1 page (1994).
Freshney, Culture of Animal Cells, A Manual of Basic Technique, Alan R. Liss, Inc., New York, 4 pages (1983).
Gura, "Cancer Models, Systems for Identifying New Drugs are Often Faulty", Science, vol. 278, 2 pages (1997).
Kodet et al., "Indole containing analogs of the natural schweinfurthins", 236th ACS National Meeting, Philadelphia PA, MEDI 421, 1 page (2008).
Kodet, "Studies on heteroaromatic schweinfurthin analogues", University of Iowa, Ph.D. Thesis, 1-275 (Dec. 2010).
Kodet et al., "Synthesis of indole analogues of the natural schweinfurthins", J. Org Chem 78 (18), 9291-9302 (2013).
Kodet et al., "Synthesis and structure activity relationships of schweinfurthin indoles", Bioorg Med Chem 22 (8), 2542-2552 (2014).
Kuder et al., "Functional Evaluation of a Fluorescent Schweinfurthin: Mechanism of Cytotoxicity and Intracellular Quantification", Molecular Pharmacology, vol. 82 (1), 9-16 (2012).
Kuder et al., "Synthesis and bilogocial activity of a fluorescent schweinfurthin analogue", Bioorganic & Medicinal Chemistry 17, 4718-4723 (2009).
MedicineNet.com, Definition of Cancer, 1 page (Aug. 29, 2006).
Mente et al., "Total Synthesis of (R,R,R)-and (S,S.S)-schweinfurthin F: Differences of bioactivity in the enantiomeric series", Bioorganic & Medicinal Chemistry Letters, 17, 911-915 (2007).

(Continued)

*Primary Examiner* — Shawquia Jackson
(74) *Attorney, Agent, or Firm* — Viksnins Harris & Padys PLLP

(57) ABSTRACT

The invention provides a compound of formula (I): wherein $R^1$-$R^5$ have any of the values defined in the specification. The compounds are useful for the treatment of cancer and other diseases.

(I)

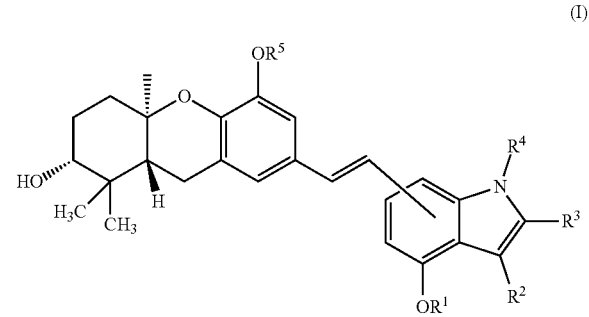

14 Claims, No Drawings

(56) References Cited

OTHER PUBLICATIONS

Mente et al., "Bf3 Et2O-Mediated Cascade Cyclizations: Synthesis of Schweinfurthins F and G", J. Org. Chem. 73, 7963-7970 (2008).
MSNBC News Services, "Mixed results on new cancer drug", 5 pages, Nov. 9, 2000.
Neighbors et al., "Synthesis of Nonracemic 3-Deoxyschweinfurthin B", J. Org. Chem., 70, 925-931 (2005).
Neighbors et al., "Synthesis and structure-activity studies of schweinfurthin B analogs: Evidence for the importance of a D-ring hydrogen bond donor in expression of differential cytotoxicity", Bioorganic & Medicinal Chemistry, 14, 1771-1784 (2006).
Neighbors et al., "Synthesis of the schweinfurthin hexahydroxanthene core through Shi epoxidation", Tetrahedron Letters, 49, 516-519 (2008).
Patent Cooperation Treaty, International Searching Authority, Search Report and Written Opinion for PCT/2013/033722, 12 pages, Jul. 8, 2013.
Thoison et al., "Vedelianin, A Hexahydroxanthene Derivative Isolated from Macaranga Vedeliana", Phytochemistry, vol. 31 (4), 1439-1442 (1992).
Topczewski et al., "Fluorescent schweinfurthin B and F analogues with anti-proliferative activity", Bioorg Med Chem 18 (18), 6734-6741 (2010).
Topczewski et al., "Exploration of Cascade Cyclizations Terminated by Tandem Aromatic Substitution: Total Synthesis of (+)-Schweinfurthin A", J. Org Chem 76, 909-919 (2011).
Topczewski et al., "Relevance of the C-5 position to schweinfurthin induced cytotoxicity", Bioorganic & Medicinal Chemistry 19, 7570-7581 (2011).
Topczewski et al., "Total Synthesis of (+)-Schweinfurthins B and E", J Org Chem 74, 6965-6972 (2009).
Treadwell et al., "A Cascade Cyclization Approach to Schweinfurthin B", Organic Letters, vol. 4 (21), 3639-3642 (2002).
Turbyville et al., "Schweinfurthin A Selectively Inhibits Proliferation and Rho Signaling in Glioma and Neurofibromatosis of type 1 Tumor Cells in an NF1-GRD Dependent Manner", Mol Cancer Ther 9(5), 1234-1243 (2010).
Ulrich et al., "Biologically active biotin derivatives of schweinfurthin F", Bioorganic & Medicinal Chemistry Letters 20, 6716-6720 (2010).
Ulrich et al., "Structural analogues of schweinfurthin F: Probing the steric, electronic, and hydrophobic properties of the D-ring substructure", Bioorganic & Medicinal Chemistry 18, 1676-1683 (2010).
Yoder et al., "Antiproliferative Prenylated Stilbenes and Flavonoids from Macaranga alnifolia from the Madagascar Rainforest", J. Nat. Prod., 70, 342-346 (2007).

* cited by examiner

SCHWEINFURTHIN ANALOGUES

RELATED APPLICATIONS

This application claims priority to U.S. Provisional Patent Application No. 61/615,725, filed on Mar. 26, 2012, the entirety of which is incorporated herein by reference.

BACKGROUND OF THE INVENTION

The family of natural products known as the schweinfurthins includes four compounds isolated from the African plant *Macaranga schweinfurthii* Pax (see Beutler, J. A. et al., *J. Nat. Prod.* 1998, 61, 1509-1512; and Beutler, J. A., et al., *Nat. Prod. Lett.* 2000, 14, 349-404). Schweinfurthins A, B, and D display significant activity in the NCI's 60-cell line anticancer assay with mean $GI_{50}$'s <1 µM. Their biological activity has attracted interest because some CNS, renal, and breast cancer cell lines are among the types most sensitive to these compounds. Inspection of the spectrum of activity shows no correlation with any currently used agents and suggests that these compounds may be acting at a previously unrecognized target or through a novel mechanism.

International Patent Application Number PCT/US2009/048690, filed 25 Jun. 2009, relates to schweinfurthin compounds that can be used as probes for elucidating the mechanism of action of these unique anti-cancer agents.

SUMMARY OF THE INVENTION

Applicant has discovered a series of modified schweinfurthin analogs that possess significant anti-cancer activity. Accordingly, in one embodiment, the invention provides a compound of formula (I):

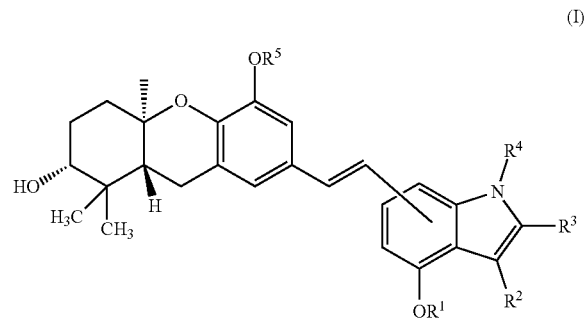

(I)

wherein:
$R^1$ is H or $(C_1-C_6)$alkyl;
$R^2$ is H, fluoro, $(C_1-C_{15})$alkyl, $(C_2-C_{15})$alkenyl, aryl, or heteroaryl, wherein any aryl or heteroaryl is optionally substituted with one or more groups independently selected from halo, nitro, trifluoromethyl, trifluoromethoxy, nitro, cyano, $(C_1-C_6)$alkyl, $(C_3-C_6)$cycloalkyl, $(C_3-C_6)$ cycloalkyl$(C_1-C_6)$alkyl, $(C_1-C_6)$alkoxy, $(C_1-C_6)$alkanoyl, $(C_1-C_6)$alkoxycarbonyl, and $(C_2-C_6)$alkanoyloxy; and wherein any $(C_1-C_{15})$alkyl, and $(C_2-C_{15})$alkenyl of $R^2$ is optionally substituted with azetidino, aziridino, pyrrolidino, piperidino, piperazino, morpholino, tetrahydrofuranyl, tetrahydrothiophenyl, $(C_3-C_6)$cycloalkyl, or $NR_aR_b$;
$R^3$ is H, $(C_1-C_{15})$alkyl, or $(C_2-C_{15})$alkenyl;
$R^4$ is H or $(C_1-C_6)$alkyl;
$R^5$ is H or $(C_1-C_6)$alkyl;
each $R_a$ and $R_b$ is independently H or $(C_1-C_6)$alkyl; and or a salt thereof.

The invention also provides a pharmaceutical composition comprising a compound of formula (I), or a pharmaceutically acceptable salt thereof, in combination with a pharmaceutically acceptable diluent or carrier.

Additionally, the invention provides a therapeutic method for treating cancer comprising administering to a mammal in need of such therapy, an effective amount of a compound of formula (I), or a pharmaceutically acceptable salt thereof.

The invention also provides a compound of formula (I) for use in medical therapy (e.g. for use in treating cancer), as well as the use of a compound of formula (I) for the manufacture of a medicament useful for the treatment of cancer in a mammal, such as a human.

The invention also provides a compound of formula (I), or a pharmaceutically acceptable salt thereof for the prophylactic or therapeutic treatment of cancer.

The invention also provides processes and intermediates disclosed herein that are useful for preparing compounds of formula (I) as well as other Schweinfurthin analogs.

DETAILED DESCRIPTION

The following definitions are used, unless otherwise described: alkyl, alkenyl, etc. denote both straight and branched groups; but reference to an individual radical such as propyl embraces only the straight chain radical, a branched chain isomer such as isopropyl being specifically referred to. Alkenyl denotes a hydrocarbon chain with one or more (1, 2, 3, or 4) double bonds. Likewise, alkynyl denotes a hydrocarbon chain with one or more (1, 2, 3, or 4) triple bonds.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The term "enantiomerically enriched" as used herein refers to mixtures that have one enantiomer present to a greater extent than another. In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20% ee; in another embodiment of the invention, the term "enantiomerically enriched" refers to a mixture having at least about 50% ee; in another embodiment of the invention, the term "enantiomerically enriched" refers to a mixture having at least about 80% ee; in another embodiment of the invention, the term "enantiomerically enriched" refers to a mixture having at least about 90% ee; in another embodiment of the invention, the term "enantiomerically enriched" refers to a mixture having at least about 95% ee; in another embodiment of the invention, the term "enantiomerically enriched" refers to a mixture having at least about 98%; in another embodiment of the invention, the term "enantiomerically enriched" refers to a mixture having at least about 99% ee.

The term "enantiomerically enriched" includes enantiomerically pure mixtures which are mixtures that are substantially free of the species of the opposite optical activity or one enantiomer is present in very low quantities, for example, 0.01%, 0.001%) or 0.0001%.

Specific values listed below for radicals, substituents, and ranges, are for illustration only; they do not exclude other defined values or other values within defined ranges for the radicals and substituents.

Specifically, $(C_1-C_{15})$alkyl can be methyl, ethyl, propyl, isopropyl, butyl, iso-butyl, sec-butyl, t-butyl, pentyl, 3-pentyl, hexyl, heptyl, octyl, nonyl, decyl, do-decyl, hexadecyl, octadecyl, icosyl; and $(C_2-C_{15})$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

In one specific embodiment the invention provides a compound of formula (1a):

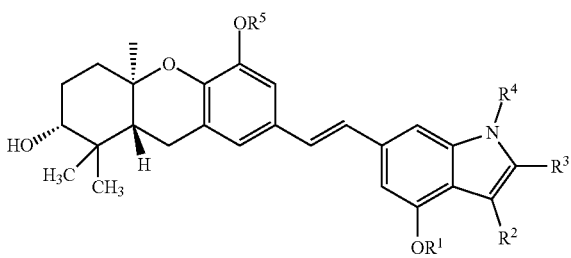

(Ia)

$R^1$ is H or $(C_1-C_6)$alkyl;
$R^2$ is H, $(C_1-C_{15})$alkyl, or $(C_2-C_{15})$alkenyl;
$R^3$ is H, $(C_1-C_{15})$alkyl, or $(C_2-C_{15})$alkenyl;
$R^4$ is H or $(C_1-C_6)$alkyl; and
$R^5$ is H or $(C_1-C_6)$alkyl;
or a pharmaceutically acceptable salt thereof.

In one specific embodiment of the invention $R^1$ is H.
In one specific embodiment of the invention $R^1$ is methyl.
In one specific embodiment of the invention $R^2$ is H.
In one specific embodiment of the invention $R^2$ is 3-methyl-2-butenyl.
In one specific embodiment of the invention $R^3$ is H.
In one specific embodiment of the invention $R^3$ is 3-methyl-2-butenyl.
In one specific embodiment of the invention $R^4$ is H.
In one specific embodiment of the invention $R^4$ is methyl.
In one specific embodiment of the invention $R^5$ is H.
In one specific embodiment of the invention $R^5$ is methyl.
In one specific embodiment of the invention R is $(C_1-C_{15})$alkyl or $(C_2-C_{15})$alkenyl.
In one specific embodiment of the invention $R^2$ is $(C_1-C_{15})$alkyl.
In one specific embodiment of the invention $R^2$ is $(C_2-C_5)$alkenyl.
In one specific embodiment of the invention:
$R^1$ is H or methyl;
one of R and R is $(C_1-C_{15})$alkyl or $(C_2-C_{15})$alkenyl, and the other is H;
$R^4$ is H or methyl; and
$R^5$ is H or methyl.

In one specific embodiment of the invention:
$R^1$ is H or methyl;
$R^2$ is $(C_1-C_{15})$alkyl or $(C_2-C_{15})$alkenyl;
$R^3$ is H;
$R^4$ is H or methyl; and
$R^5$ is H or methyl.

In a further embodiment of the foregoing, $R^2$ is $(C_1-C_{15})$alkyl.
In a further embodiment of the foregoing, $R^2$ is $(C_2-C_5)$alkenyl.
In a further embodiment of the foregoing, $R^2$ is 3-methyl-2-butenyl.
In a further embodiment of the foregoing, $R^2$ is $(C_{10})$alkenyl.
In a further embodiment of the foregoing, $R^2$ is $(C_{15})$alkenyl.

In one specific embodiment of the invention:
$R^1$ is H or methyl;
$R^2$ is H;
$R^3$ is $(C_1-C_{15})$alkyl or $(C_2-C_{15})$alkenyl;
$R^4$ is H or methyl; and
$R^5$ is H or methyl.

In a further embodiment of the foregoing, $R^3$ is $(C_5)$alkenyl.
In a further embodiment of the foregoing, $R^3$ is 3-methyl-2-butenyl.
In one specific embodiment of the invention $R^2$ is $(C_5)$alkenyl.
In one specific embodiment of the invention $R^2$ is $(C_{15})$alkenyl.
In one specific embodiment of the invention $R^2$ is phenyl, 4-fluorophenyl, or 2-methyl-2(H)-indazol-4-yl.
In one specific embodiment of the invention $R^2$ is a 5-membered heteroaryl optionally substituted with one or more groups independently selected from halo, nitro, trifluoromethyl, trifluoromethoxy, nitro, cyano, $(C_1-C_6)$alkyl, $(C_3-C_6)$cycloalkyl, $(C_3-C_6)$cycloalkyl$(C_1-C_6)$alkyl, $(C_1-C_6)$alkoxy, $(C_1-C_6)$alkanoyl, $(C_1-C_6)$alkoxycarbonyl, and $(C_2-C_6)$alkanoyloxy.
In one specific embodiment of the invention R is a 5-membered heteroaryl optionally substituted with one or more groups independently selected from $(C_1-C_6)$alkyl.
In one specific embodiment of the invention $R^2$ is thienyl, pyrrolyl, furanyl, pyrazolyl, isoxazolyl, or thiazolyl, which R is optionally substituted with one or more groups independently selected from $(C_1-C_6)$alkyl.
In one specific embodiment of the invention:
$R^1$ is H or methyl;
$R^2$ is a 5-membered heteroaryl optionally substituted with one or more groups independently selected from halo, nitro, trifluoromethyl, trifluoromethoxy, nitro, cyano, $(C_1-C_6)$alkyl, $(C_3-C_6)$cycloalkyl, $(C_3-C_6)$cycloalkyl$(C_1-C_6)$alkyl, $(C_1-C_6)$alkoxy, $(C_1-C_6)$alkanoyl, $(C_1-C_6)$alkoxycarbonyl, and $(C_2-C_6)$alkanoyloxy;
$R^3$ is H;
$R^4$ is H or methyl; and
$R^5$ is H or methyl.

In a further embodiment of the foregoing, $R^2$ is a 5-membered heteroaryl optionally substituted with one or more groups independently selected from $(C_1-C_6)$alkyl.
In a further embodiment of the foregoing, $R^2$ is thienyl, pyrrolyl, furanyl, pyrazolyl, isoxazolyl, or thiazolyl, which $R^2$ is optionally substituted with one or more groups independently selected from $(C_1-C_6)$alkyl.

In one specific embodiment of the invention R² is (C₁-C₆)alkyl, which is optionally substituted with azetidino, aziridino, pyrrolidino, piperidino, piperazino, morpholino, or NR_aR_b.

In one specific embodiment of the invention:
R¹ is H or methyl;
R² is (C₁-C₆)alkyl, which is optionally substituted with azetidino, aziridino, pyrrolidino, piperidino, piperazino, morpholino, or NR_aR_b; each R_a and R_b is independently H or (C₁-C₆)alkyl;
R³ is H;
R⁴ is H or methyl; and
R⁵ is H or methyl.

In one specific embodiment of the invention:
R¹ is H or methyl;
R² is phenyl or indazolyl, either of which is optionally substituted with one or more groups independently selected from halo, nitro, trifluoromethyl, trifluoromethoxy, nitro, cyano, (C₁-C₆)alkyl, (C₃-C₆)cycloalkyl, (C₃-C₆)cycloalkyl(C₁-C₆)alkyl, (C₁-C₆)alkoxy, (C₁-C₆)alkanoyl, (C₁-C₆)alkoxycarbonyl, and (C₂-C₆)alkanoyloxy;
R³ is H;
R⁴ is H or methyl; and
R⁵ is H or methyl.

In one specific embodiment of the invention R¹ is methyl; R² is phenyl, 4-fluorophenyl, or 2-methyl-2(H)-indazol-4-yl; R³ is H; and R⁴ is methyl.

In one specific embodiment of the invention R³ is (C₁-C₁₅)alkyl or (C₂-C₁₅)alkenyl.

In one specific embodiment of the invention R³ is (C₅)alkenyl.

In one specific embodiment of the invention R² is (C₁₀)alkenyl.

In one specific embodiment of the invention R² is (C₁₅)alkenyl.

In one specific embodiment of the invention R⁴ is (C₁-C₆)alkyl.

In one specific embodiment of the invention R⁴ is methyl.

In one specific embodiment of the invention the compound of formula (I) is selected from:

6

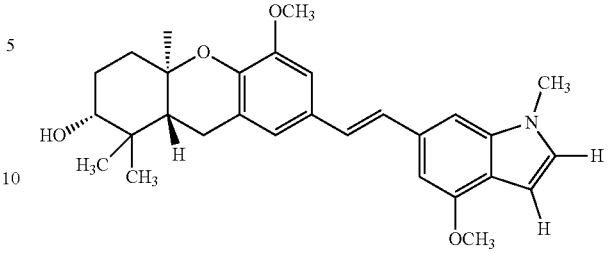

7

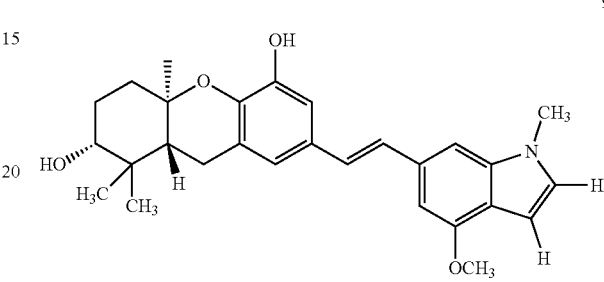

8

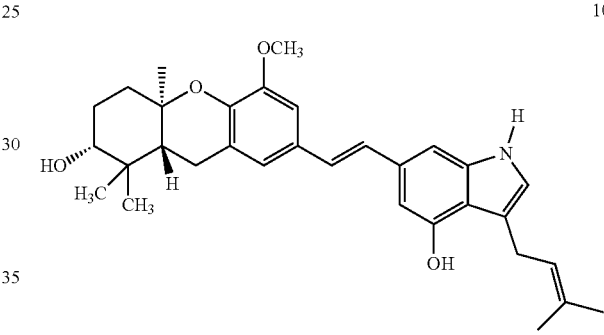

9

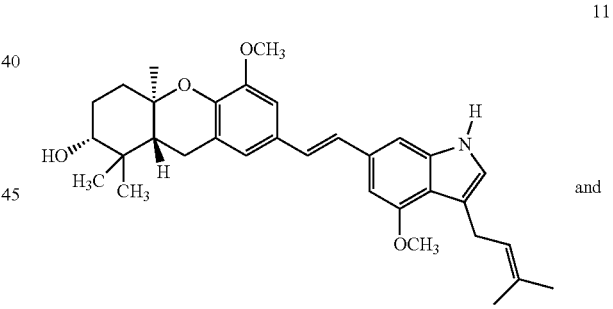

10

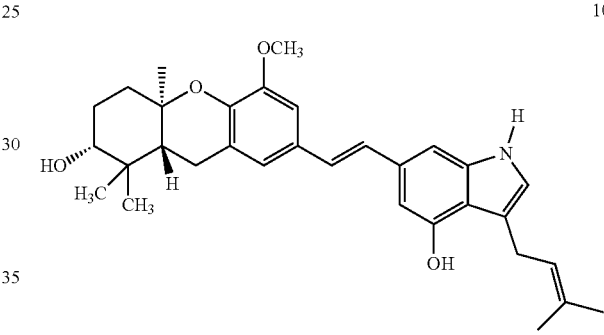

11

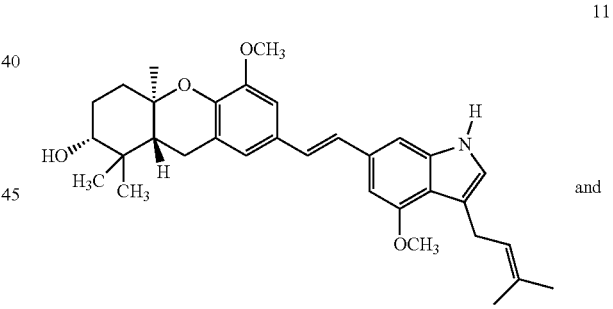

and

12 and salts thereof.

In one specific embodiment of the invention the compound of formula (I) is selected from:

13
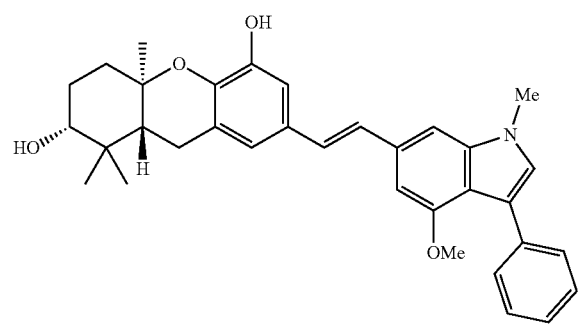
14
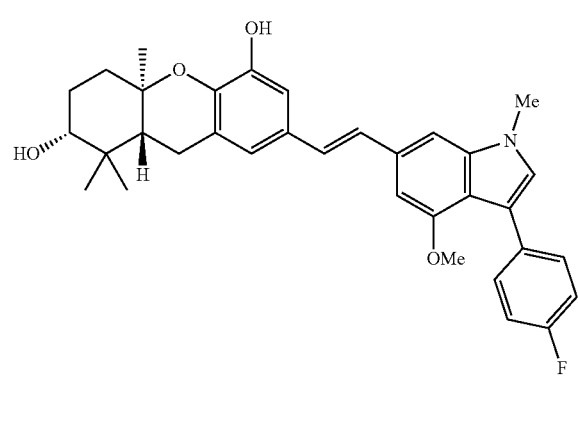
15
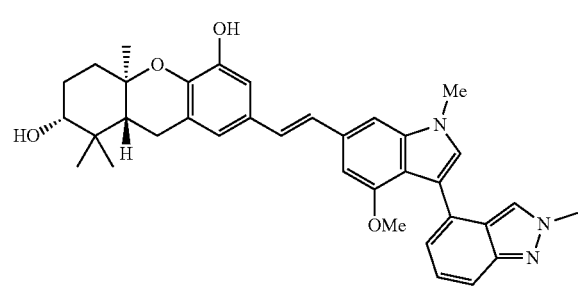
and salts thereof.
In one specific embodiment of the invention the compound of formula (I) is selected from:
16
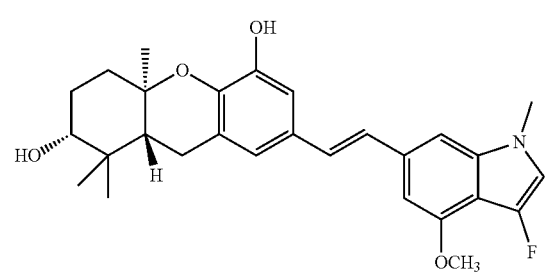
17
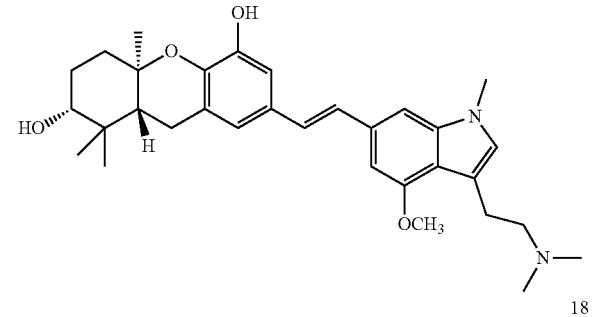
18
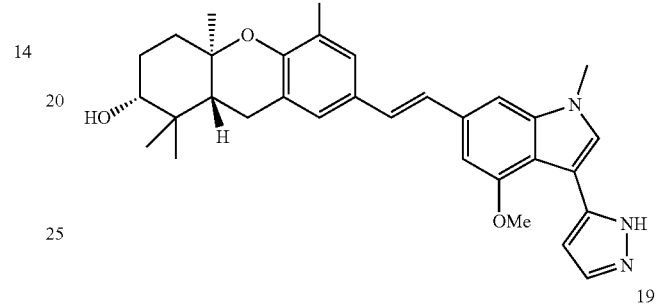
19
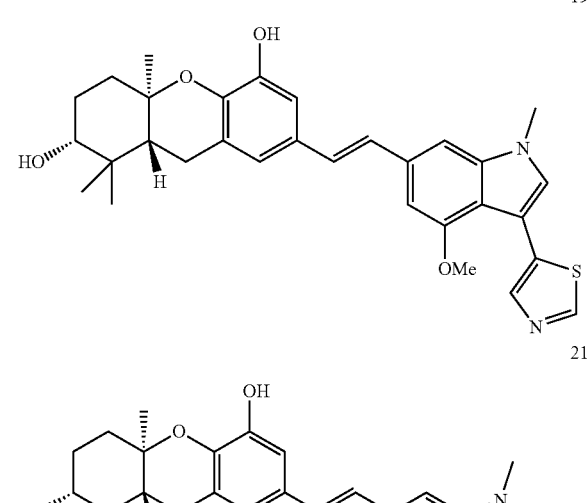
20
21
22
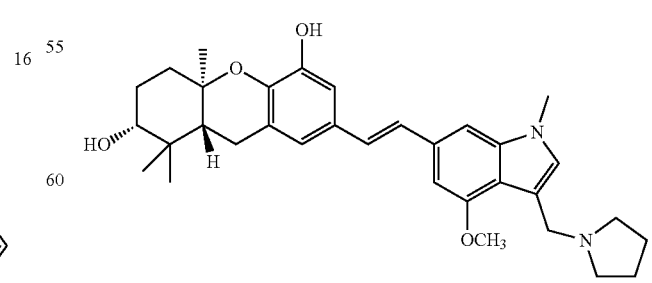
In one specific embodiment the invention provides a compound of formula (I):

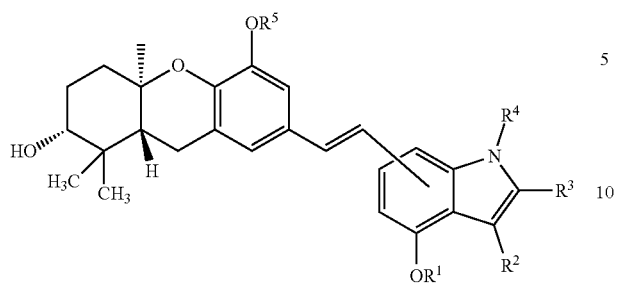

(I)

wherein:

R¹ is H or (C₁-C₆)alkyl;

R² is H, (C₁-C₁₅)alkyl, (C₂-C₁₅)alkenyl, aryl, or heteroaryl, wherein any aryl or heteroaryl is optionally substituted with one or more groups independently selected from halo, nitro, trifluoromethyl, trifluoromethoxy, cyano, (C₁-C₆)alkyl, (C₃-C₆)cycloalkyl, (C₃-C₆) cycloalkyl(C₁-C₆)alkyl, (C₁-C₆)alkoxy, (C₁-C₆)alkanoyl, (C₁-C₆)alkoxycarbonyl, and (C₂-C₆) alkanoyloxy;

R³ is H, (C₁-C₁₅)alkyl, or (C₂-C₁₅)alkenyl;

R⁴ is H or (C₁-C₆)alkyl; and

R⁵ is H or (C₁-C₆)alkyl;

or a salt thereof.

In one specific embodiment of the invention the compound of formula (I) is isolated and purified.

In one specific embodiment the invention provides a compound which is enantiomerically enriched and has an enantiomeric excess of at least about 90%.

In one specific embodiment the invention provides a compound which is enantiomerically enriched and has an enantiomeric excess of at least about 95%.

In one specific embodiment the invention provides a compound which is enantiomerically enriched and has an enantiomeric excess of at least about 98%.

In one specific embodiment the invention provides a compound which is enantiomerically enriched and has an enantiomeric excess of at least about 99%.

In one specific embodiment the invention provides a compound which is enantiomerically pure.

In one specific embodiment the invention provides a compound of formula (I) which is the 2R 4aR 9aR enantiomer.

In one specific embodiment the compound of formula (I) is not:

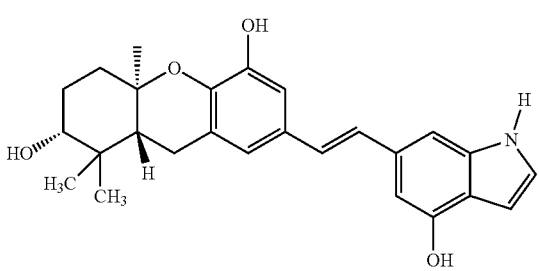

1

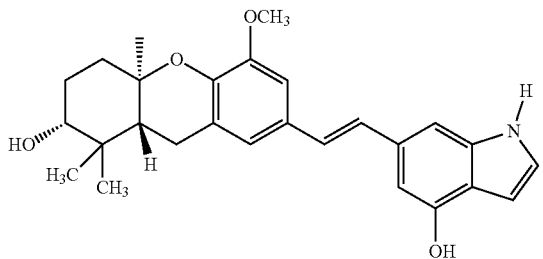

2

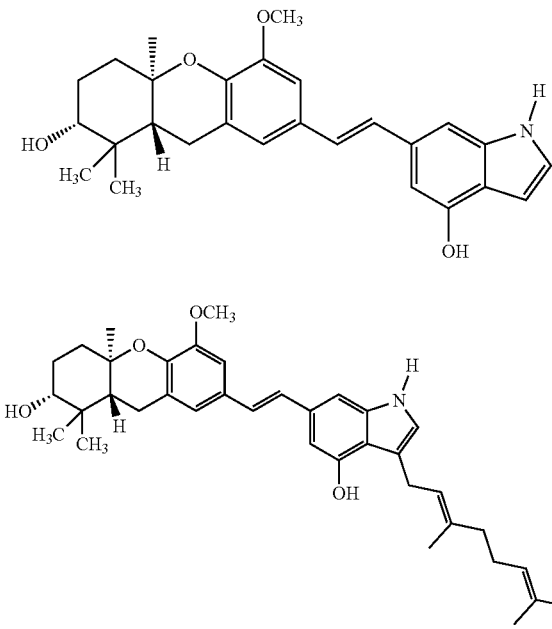

3

4

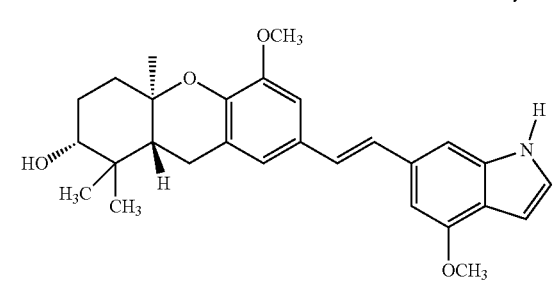

5

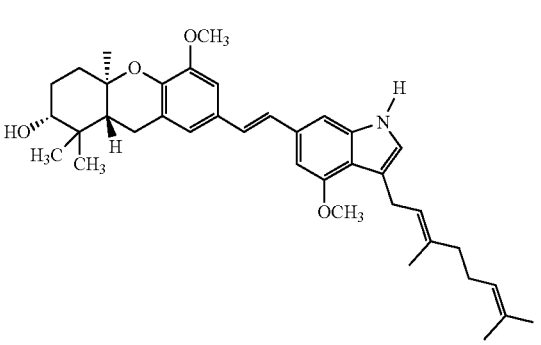

or

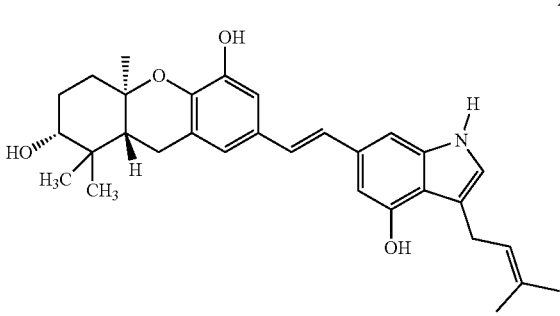

20

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Suitable acids includes any organic acid suitable to catalyze the reaction, such as, trifluoroacetic acid (TFA). Suitable base includes any base suitable to catalyze the reaction, such as, triethyl amine (TEA).

As used herein, the terms "isolated" and "purified" refer to substances that are substantially free of other biological agents, for example, at least about 95%, about 98%, or about 99% pure.

As used herein, the terms "treat," "treatment," and "treating," extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate.

Compounds and pharmaceutical compositions suitable for use in the present invention include those wherein the active compound is administered in an effective amount to achieve its intended purpose. More specifically, a "therapeutically effective amount" means an amount effective to treat the disease, disorder, and/or condition. Determination of a therapeutically effective amount is well within the capacity of persons skilled in the art, especially in light of the detailed disclosure provided herein.

The pharmaceutically active compounds of the invention can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form for injection or infusion should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form. However, it will generally be desirable to administer them to the skin as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the pharmaceutically active compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the pharmaceutically active compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compounds of the invention can also be administered in combination with other therapeutic agents that are effective to treat cancer.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

General Synthetic Methods

Generally, a compound of formula (I) can be prepared by coupling an aldehyde of formula 100 with a phosphonate of formula 101,

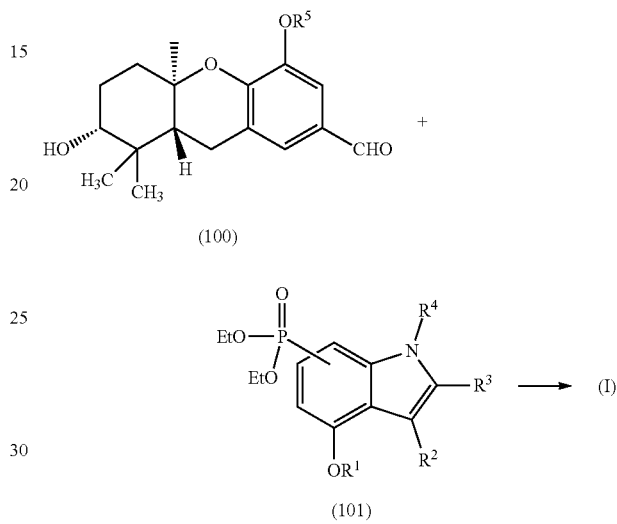

wherein $R^1$-$R^5$ have any of the values or specific values defined herein.

An intermediate compound of formula (101a):

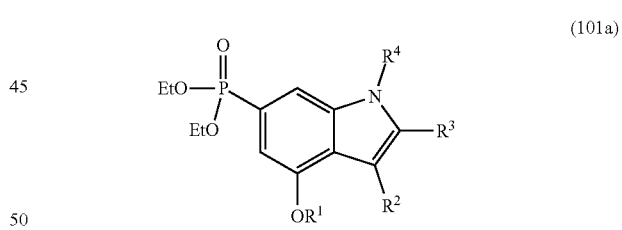

is useful for preparing compounds of formula (Ia).

A compound of formula (I) wherein $R^2$ is an alkyl group substituted with an amine, for example as in Compounds 17, 20, and 21, can be prepared as illustrated below.

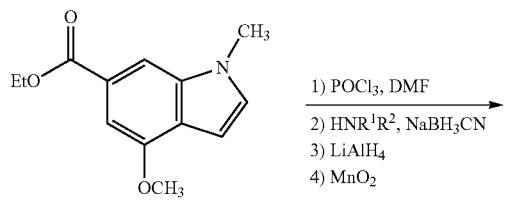

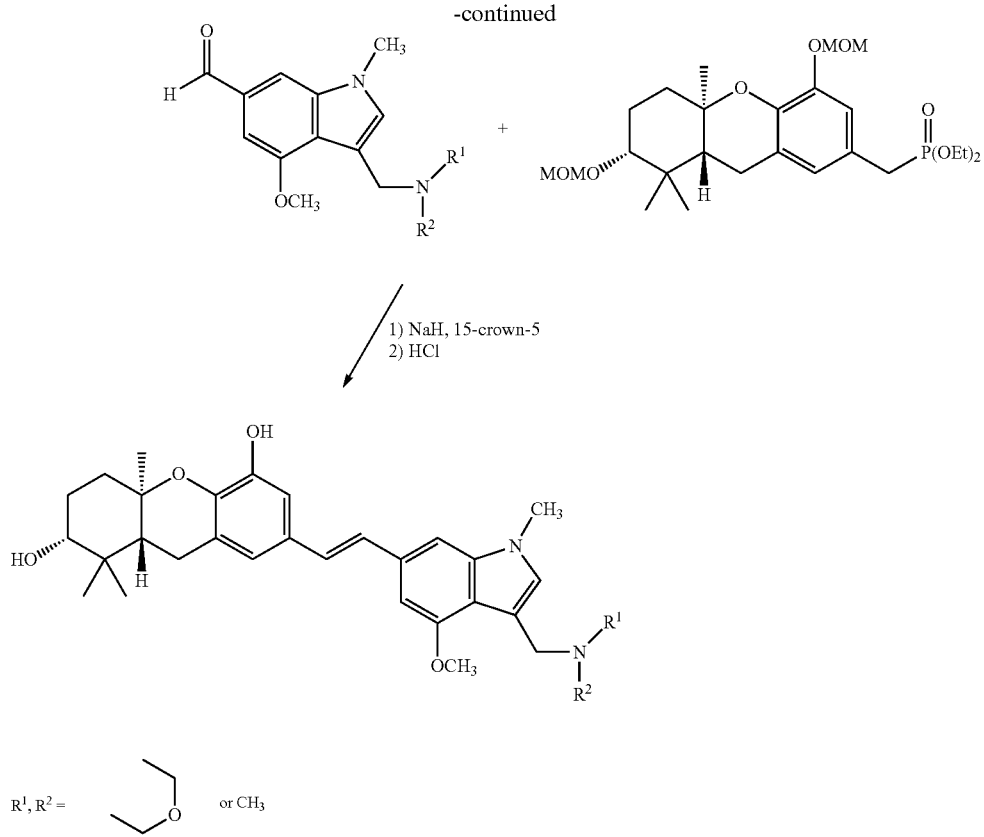
A compound of formula (I) wherein $R^2$ is a heteroaryl group can be prepared as illustrated below, wherein the ring containing A, B, C, and D represents a heteroaryl ring, for example as in Compounds 18 and 19.
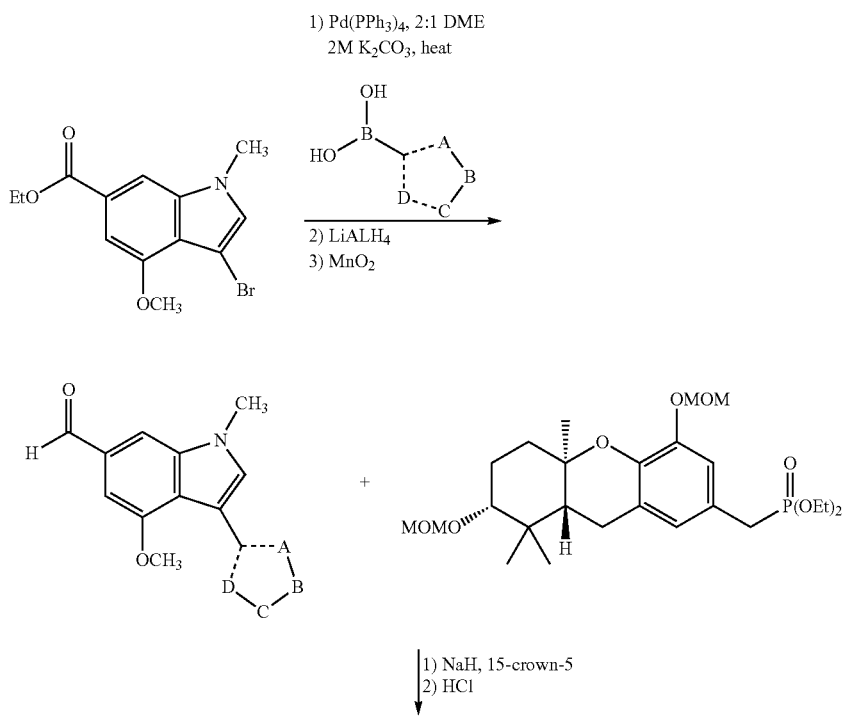

-continued

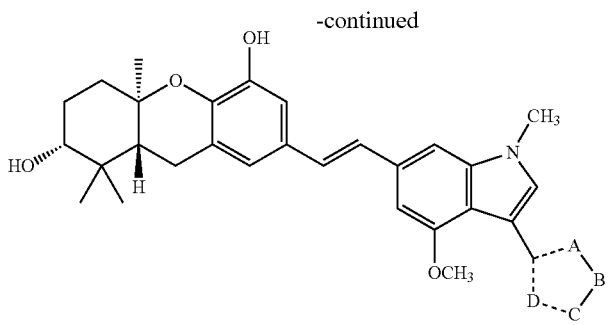

In a specific embodiment, the ring containing A, B, C and D represents a ring selected from the group consisting of:

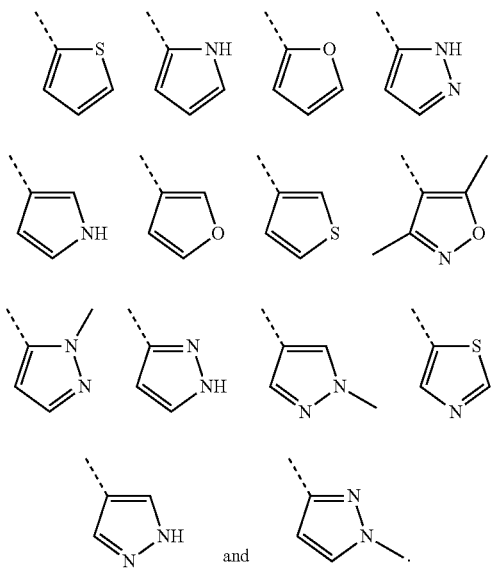

and.

The anti-cancer activity of a compound of the invention may be determined using pharmacological models which are well known to the art, for example, NCI 60-cell line anti-cancer assay. Representative compounds of formula (I) were tested and were found to have anti-cancer activity in this assay.

The anti-cancer effect of a compound of the invention can also be determined using the assay scheme discussed in Test A below.

Test A

The National Cancer Institute 60 human tumor cell line anti-cancer assay has been used for indicating the schweinfurthin-like activity of various analogues. Additionally, a three pronged approach that allows a more rapid turn around can be used. This three pronged testing scheme involves 1) MTT assay in schweinfurthin sensitive human glioma derived SF-295 cell line; 2) MTT assay in the schweinfurthin resistant human non-small cell lung cancer derived cell line A549; and 3) microscopic observation of cell morphology changes at 24 and 48 hours. Compounds displaying schweinfurthin-like activity show a dramatic change in cell morphology at concentrations consistent with anti-cancer activity. This three pronged testing scheme is a very simple method that has successfully identified compounds with and without schweinfurthin-like activity. Accordingly, in one embodiment the invention provides a method for identifying a compound with schweinfurthin-like activity comprising, subjecting the compound to 1) an MTT assay in a schweinfurthin sensitive human glioma derived SF-295 cell line; 2) an MTT assay in the schweinfurthin resistant human non-small cell lung cancer derived cell line A549; and 3) a microscopic observation of cell morphology changes at one or more preselected time points (e.g. at about 24 or 48 hours).

| Compound | SF-295 | A549 |
|----------|--------|------|
| 6        | 2.39   | >10  |
| 7        | 0.47   | >10  |
| 8        | 0.2    | >10  |
| 9        | 0.02   | >10  |
| 10       | 0.05   | 3    |
| 11       | 0.19   | 1.3  |
| 12       | 0.02   | 0.8  |
| 13       | 0.02   | >10  |
| 14       | 0.04   | 10   |
| 15       | 0.05   |      |

Compounds 7, 9, and 10 have been tested for solubility and permeability using a kinetic solubility screen and a CACO-2 cell permeability assay and they show improved solubility or permeability compared to Compound 4 (wherein $R^2$, $R^3$, and $R^4$ are each H). Additionally, Compound 4 has been found to be an efflux pump substrate. For the treatment of certain diseases, it may be beneficial to have a therapeutic agent that is not an efflux pump substrate. Representative compounds of the invention (e.g. Compounds 7, 9, and 10) have been tested and found to possess diminished activity as efflux pump substrates compared to Compound 4. Accordingly, compounds of formula I wherein at least one of $R^2$, $R^3$, and $R^4$ is other than H may possess diminished activity as efflux pump substrates and thus be particularly useful as therapeutic agents. In one embodiment of the invention $R^2$ is $(C_1-C_{15})$alkyl or $(C_2-C_{15})$ alkenyl. In one embodiment of the invention $R^4$ is $(C_1-C_{15})$alkyl or $(C_2-C_{15})$alkenyl. In one embodiment of the invention $R^4$ is $(C_1-C_6)$alkyl.

The invention will now be illustrated by the following non-limiting Examples.

EXAMPLES

Example 1

Synthesis of Compound 10

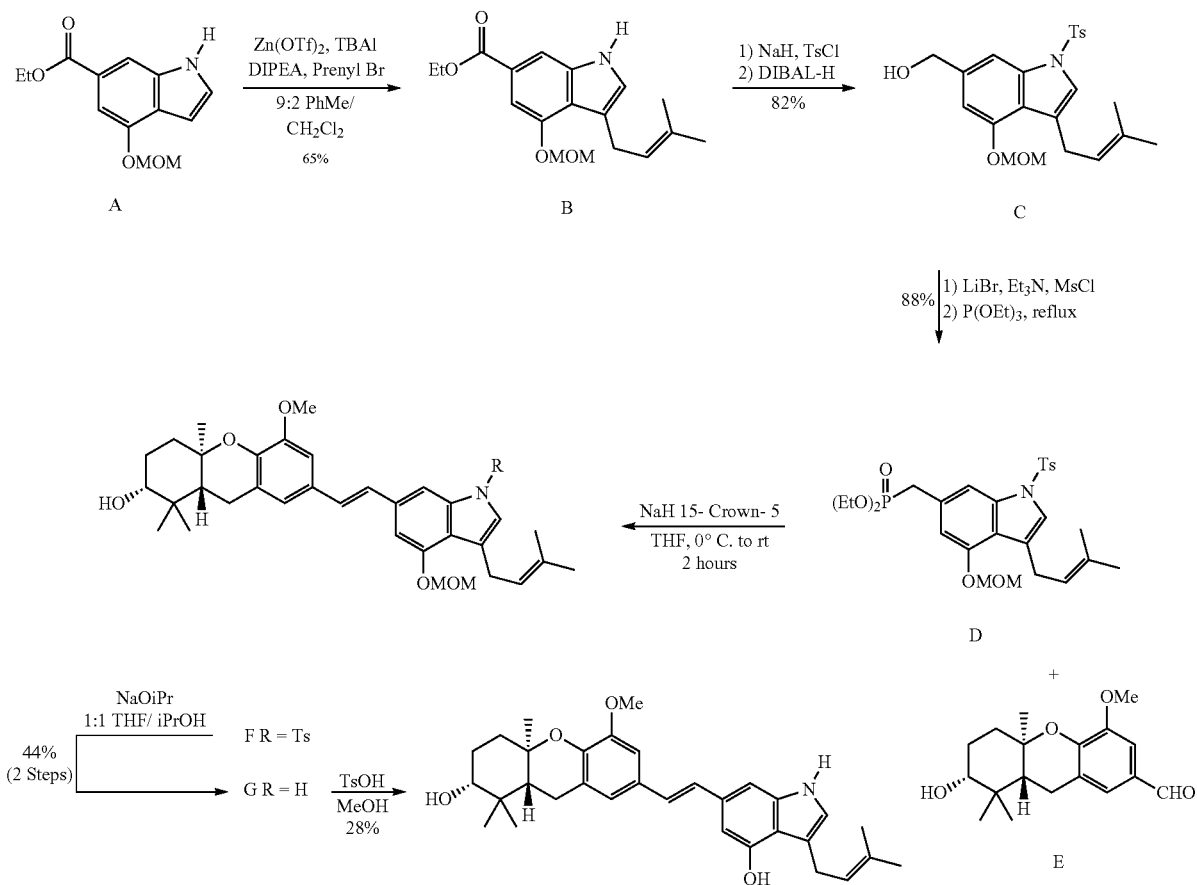

Synthesis of B.

To indole A (1.00 g, 4.01 mmol), TBAI (739 mg, 2.00 mmol), and Zn(OTf)$_2$ (878 mg, 2.41 mmol) in a 9:2 mixture of toluene and CH$_2$Cl$_2$ (22 mL) at it was added DIPEA (0.77 mL, 4.41 mmol) and the reaction mixture was allowed to stir for 10 min. Prenyl bromide (298 mg, 2.00 mmol) was added dropwise. After 3 hours the reaction mixture was quenched by addition of NH$_4$Cl (sat) and extracted with EtOAc. The combined organic extracts were washed with H$_2$O, dried (MgSO$_4$), and filtered, and the filtrate concentrated in vacuo. Final purification by flash column chromatography (10% to 15% EtOAc in hexanes) afforded prenylated indole B (415 mg 65%) along with recovered starting material A (540 mg): $^1$H NMR δ 8.47 (br s, 1H), 7.79 (d, J=1.2 Hz, 1H), 7.34 (d, J=1.1 Hz, 1H), 6.96 (m, 1H), 5.46 (m, 1H), 5.35 (s, 2H), 4.37 (q, J=7.1 Hz, 2H), 3.65 (d, J=6.6 Hz, 2H), 3.53 (s, 3H) 1.74 (d, J=1.0 Hz, 3H), 1.72 (s, 3H), 1.38 (t, J=7.1 Hz, 3H); $^{13}$C δ 167.6, 151.4, 137.4, 131.5, 124.6, 123.8, 123.7, 121.3, 116.7, 108.2, 102.6, 94.2, 60.7, 56.2, 25.7, 25.4, 17.7, 14.4; HRMS (EI$^+$) calcd for C$_{18}$H$_{23}$NO$_4$ [M$^+$] 317.1627; found 317.1631.

Alcohol C.

To indole B (315 mmol, 0.99 mmol) in THF at 0° C. was added NaH (50 mg, 1.25 mmol, 60% dispersion oil) and the reaction mixture was allowed to stir for 10 min. After TsCl (230 mg, 1.21 mmol) was added, the solution was stirred for 30 min and DIBAL-H (0.71 mL, 4.0 mmol) was added dropwise. After an additional 30 min the reaction was quenched with NH$_4$Cl (sat) acidified with HCl, and extracted with EtOAc. The combined organic extracts were washed with Na$_2$CO$_3$ (sat), brine, dried (MgSO$_4$), and filtered, and the filtrate was concentrated in vacuo. Purification by flash column chromatography (34% EtOAc in hexanes) afforded benzylic alcohol C (348 mg, 82%): $^1$H NMR δ 7.71 (d, J=8.4 Hz, 2H), 7.60 (s, 1H), 7.16 (d, J=8.2 Hz, 2H), 7.13 (m, 1H), 6.85 (d, J=0.6 Hz, 1H), 5.41-5.39 (m, 1H), 5.22 (s, 2H), 4.71 (s, 2H), 3.51 (d, J=7.1 Hz, 2H) 3.46 (s, 3H) 2.37 (br s, 1H), 2.30 (s, 3H), 1.76 (d, J=0.8 Hz, 3H), 1.68 (s, 3H); $^{13}$C NMR δ 151.8, 144.6, 139.1, 137.0, 135.2, 132.9, 129.7 (2C), 126.6 (2C), 122.7, 121.9, 121.8, 120.2, 105.9, 105.7, 94.1, 65.5, 56.1, 25.7, 25.6, 21.4, 17.7; HRMS (EI$^+$) calcd for C$_{23}$H$_{27}$NO$_5$S [M$^+$] 429.1610. found 429.1609.

Indole phosphonate D.

To alcohol C (332 mg) in THF (15 mL) at 0° C. was added LiBr (537 mg, 6.18 mmol) and Et$_3$N (0.43 mL, 3.09 mmol). The solution was stirred for 5 min and then MsCl (0.18 mL, 2.32 mmol) was added dropwise. The reaction was allowed to warm to rt, and after 2 hours it was quenched by addition of saturated NaHCO$_3$ and extracted with EtOAc. The combined organic extracts were washed with brine, dried (MgSO$_4$), and filtered, and the filtrate was concentrated in vacuo. The resulting residue was dissolved in P(OEt)$_3$ (3 mL) and was heated to reflux. The next day the solution was allowed to cool to rt then poured into water and extracted with EtOAc. The organic extracts was washed with brine, dried (MgSO$_4$), and concentrated in vacuo. Final purification by flash column chromatography (2% EtOH in Et$_2$O) afforded indole phosphonate D (374 mg, 88%) as a white waxy solid: $^1$H NMR δ 7.75 (d, J=8.4 Hz, 2H), 7.57 (m, 1H), 7.21 (d, J=8.1 Hz, 2H), 7.10, (d, J=1.1 Hz, 1H), 6.80 (m, 1H), 5.41-5.36 (m, 1H), 5.23 (s, 2H), 4.00 (m, 4H), 3.51-3.47 (m, 5H), 3.22 (d, J$_{PH}$=21.5 Hz, 2H), 2.33 (s, 3H), 1.77 (s, 3H), 1.68 (s, 3H), 1.25 (t, J=7.0 Hz, 6H); $^{13}$C NMR δ 151.6 (d, J$_{CP}$=2.9 Hz) 144.8, 137.1 (d, J$_{CP}$=3.1 Hz), 135.4, 133.0, 129.7 (2C), 129.2 (d, J$_{CP}$=9.3 Hz), 126.8 (2C), 122.7 (d, J$_{CP}$=1.6 Hz), 121.8, 121.7 (d, J$_{CP}$=1.8 Hz), 119.7 (d, J$_{CP}$=3.2 Hz), 108.9 (d, J$_{CP}$=5.9 Hz), 108.7 (d, J$_{CP}$=7.6 Hz), 94.3, 62.1 (d, J$_{CP}$=6.7 Hz, 2C), 56.1, 34.2 (d, J$_{CP}$=138.3 Hz), 25.7, 25.6, 21.4, 17.7, 16.3 (d, J$_{CP}$=6.0 Hz, 2C); $^{31}$P NMR δ 26.9; HRMS (EI$^+$) calcd for C$_{27}$H$_{36}$NO$_7$PS [M$^+$] 549.1950. found 549.1959.

Protected Analogue G.

To aldehyde E (44 mg, 0.15 mmol) and phosphonate D (100 mg, 0.182 mmol) in THF (4 mL) at 0° C. was added NaH (80 mg, 2.0 mmol, 60% dispersion oil) and 15-Crown-5 (2 drops). The reaction mixture was allowed to stir for 2 hours. It was then quenched by addition of NH$_4$Cl (sat) and extracted with EtOAc. The combined organic layers were washed with brine, dried (MgSO$_4$), and filtered and the filtrate was concentrated in vacuo. Purification by flash column chromatography (50% EtOAc in hexanes) afforded a mixture of N-Ts protected analogue F and unprotected indole analogue G (55 mg) as an oil. The resulting mixed residue was dissolved in a 1:1 mixture of THF and 2-propanol (5 mL) at 0° C. and to it was added NaH (150 mg, excess) and the reaction mixture was allowed to warm to rt. The following day the reaction mixture was quenched by addition of water and extracted with EtOAc. The combined organic extracts were washed with brine, dried (MgSO$_4$), and filtered, and the filtrate was concentrated in vacuo. Final purification by flash column chromatography (50% EtOAc in hexanes) afforded analogue G (35 mg, 0.064 mmol) as an oil: $^1$H NMR δ 7.95 (br s, 1H), 7.07 (s, 1H), 6.99-6.98 (m, 2H), 6.92-6.90 (m, 2H), 6.87 (m, 1H), 6.81 (s, 1H), 5.51-5.46 (m, 1H), 5.36 (s, 2H), 3.90 (s, 3H), 3.62 (d, J=7.0 Hz, 2H), 3.57 (s, 3H), 3.43 (dd, J=11.6, 3.8 Hz, 1H), 2.74-2.71 (m, 2H), 2.15-2.10 (m, 1H), 1.89-1.56 (m, 11H), 1.26 (s, 3H), 1.11 (s, 3H), 0.89 (s, 3H); $^{13}$C NMR δ 152.1, 148.9, 142.3, 138.6, 133.0, 131.2, 129.4, 127.6, 126.8, 124.1, 122.6, 120.9, 120.2, 117.5, 116.7, 106.9, 103.8, 100.9, 94.3, 78.0, 77.0, 56.1, 56.0, 46.8, 38.4, 37.7, 28.3, 27.3, 25.7, 25.6, 23.2, 19.8, 17.7, 14.3; HRMS (EI$^+$) calcd for C$_{34}$H$_{43}$NO$_4$ [M$^+$] 545.3141. found 545.3135.

Compound 10.

To analogue G (31 mg, 0.057 mmol) in MeOH (2 mL) at rt was added TsOH (75 mg, 0.39 mmol) and the reaction flask was wrapped in foil. After 10 hours the reaction was quenched by pouring into NaHCO$_3$ (sat) and extracted with EtOAc. The combined organic extracts were washed with Na$_2$CO$_3$ (sat), brine, and dried (MgSO$_4$), filtered, and the filtrate was concentrated in vacuo. Final purification by flash column chromatography (50% EtOAc in hexanes) afforded Compound 10 (8 mg, 28%) as a light yellow oil: $^1$H NMR δ 7.90 (br s 1H), 6.99-6.96 (m, 3H), 6.89-6.85 (m, 3H), 6.74 (s, 1H), 5.91 (br s, 1H), 5.54 (m, 1H), 3.90 (s, 3H), 3.58 (d, J=6.6 Hz, 2H), 3.44 (dd, J=11.6, 3.7 Hz, 1H), 2.75-2.72 (m, 2H), 2.16-2.10 (m, 1H), 1.90-1.55 (m, 5H), 1.84 (s, 3H), 1.82 (s, 3H), 1.26 (s, 3H), 1.11 (s, 3H), 0.89 (s, 3H); $^{13}$C NMR δ 150.1, 148.9, 139.2, 135.1, 133.6, 129.8, 129.4, 127.3, 127.1, 125.1, 122.6, 121.0, 120.3, 116.4, 115.2, 106.9, 102.8, 102.8, 78.1, 56.0, 46.8, 38.4, 37.7, 28.3, 27.4, 25.8, 25.7, 23.2, 19.8, 17.7, 14.3; HRMS (EI$^+$) calcd for C$_{32}$H$_{39}$NO$_4$ [M$^+$] 501.2879. found 501.2874.

Example 2

Synthesis of Compound 6

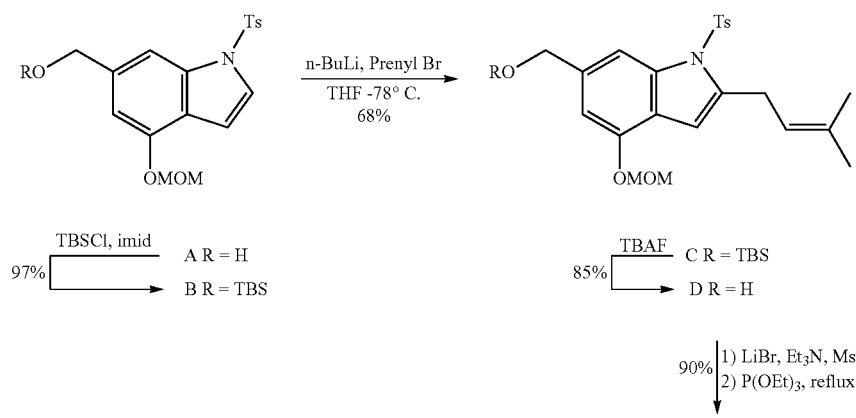

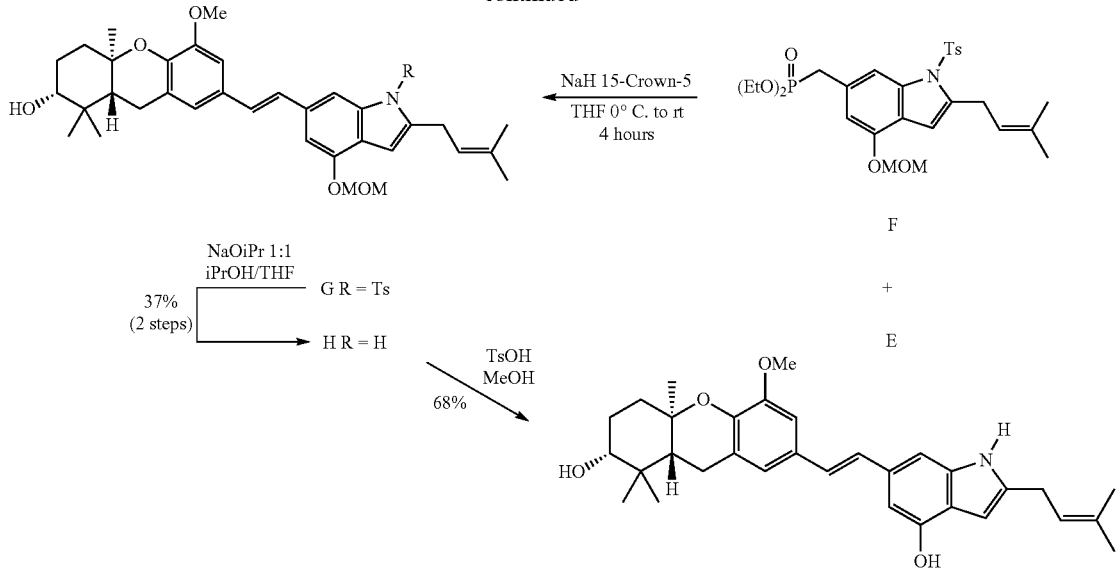

Silyl Protected Alcohol B.

To alcohol A (1.09 g, 3.01 mmol) in CH$_2$Cl$_2$ (50 mL) at 0° C. was added imidazole (502 mg, 7.53 mmol) and TBSCl (500 mg, 3.31 mmol) and then the solution was allowed to warm to rt. The next day the reaction was quenched by addition of NH$_4$Cl (sat), and extracted with CH$_2$Cl$_2$. The combined organic extracts were washed with brine, dried (MgSO$_4$), and filtered, and the filtrate was concentrated in vacuo. Final purification by flash column chromatography (8% EtOAc in hexanes) afforded silyl protected alcohol B (1.39 g, 97%): $^1$H NMR δ 7.75 (d, J=8.4 Hz, 2H), 7.63 (m, 1H), 7.45 (d, J=3.7 Hz, 1H), 7.20, (dd, J=8.5, 0.6 Hz, 2H), 6.88 (m, 1H), 6.73 (dd, J=3.7, 0.8 Hz, 1H), 5.24 (s, 2H), 4.81 (s, 2H), 3.47 (s, 3H), 2.33 (s, 3H), 0.97 (s, 9H), 0.12 (s, 6H); $^{13}$C δ 150.3, 144.8, 139.8, 136.1, 135.3, 129.8 (2C), 168.8 (2C), 124.9, 120.7, 105.8, 105.9, 104.9, 94.7, 65.2, 56.1, 25.9 (3C), 21.5, 18.3, −5.2 (2C); HRMS (EI$^+$) calcd for C$_{29}$H$_{41}$NO$_5$SSi [M$^+$] 475.1849. found 475.1856.

Prenylated Indole C.

To silyl protected indole B (724 mmol, 1.52 mmol) in THF was added a few 4 Å molecular sieves and the mixture was cooled to −78° C. After n-BuLi (0.75 ml, 2.3M in hexanes) was added, the mixture was stirred for 20 min and prenyl bromide (420 mmol, 2.82 mmol) was added. The next day the reaction mixture was quenched by addition of NH$_4$Cl (sat), and extracted with Et$_2$O. The combined organic layers were washed with brine, dried (MgSO$_4$), and filtered, and the filtrated was concentrated in vacuo. Final purification by flash column chromatography (5% EtOAc in hexanes) afforded prenyl indole C (560 mg, 68%) as well as recovered starting material (76 mg, 10%): $^1$H NMR δ 7.91 (d, J=0.8 Hz, 1H), 7.73 (d, J=8.4 Hz, 2H), 7.25, (d, J=8.5 Hz, 2H), 6.99 (s, 1H), 6.52 (d, J=0.8 Hz, 1H), 5.47 (m, 1H), 5.31 (s, 2H), 4.90 (s, 2H), 3.74 (d, J=7.2 Hz, 2H), 3.55 (s, 3H), 2.40 (s, 3H), 1.86 (s, 3H), 1.71 (s, 3H) 1.05 (s, 9H), 0.20 (s, 6H); $^{13}$C NMR δ 149.5, 144.5, 139.9, 138.7, 138.6, 136.5, 134.5, 129.7 (2C), 126.3 (2C), 119.8, 119.6, 106.5, 106.3, 105.3, 94.8, 65.5, 56.0, 27.9, 25.9 (3C), 25.7, 21.4, 18.3, 17.7, −5.2 (2C); HRMS (EI$^+$) calcd for C$_{29}$H$_{41}$NO$_5$SSi [M$^+$] 543.2475. found 543.2476.

Alcohol D.

To silyl protected alcohol C (682 mg, 1.26 mmol) in THF (20 mL) at rt was added TBAF (1.88 mL, 1.0 M in THF). After 2 hours the reaction was quenched with H$_2$O and extracted with EtOAc. The combined organics were washed with brine, dried (MgSO$_4$), and filtered, and the solvent was removed in vacuo. Purification by flash column chromatography (30 to 45% EtOAc in hexanes) afforded alcohol D (461 mg, 85%): $^1$H NMR δ 7.84 (s, 1H), 7.74 (d, J=8.3 Hz, 2H), 7.17, (d, J=8.4 Hz, 2H), 6.93 (s, 1H), 6.44 (s, 1H), 5.38 (m, 1H), 5.24 (s, 2H), 4.74 (s, 2H), 3.64 (d, J=7.1 Hz, 2H), 3.46 (s, 3H), 2.60 (br s, 1H), 2.31 (s, 3H), 1.78 (s, 3H), 1.61 (s, 3H); $^{13}$C δ 149.5, 144.6, 140.1, 138.5, 138.1, 136.2, 134.7, 129.7 (2C), 126.2 (2C), 119.9, 119.5, 107.2, 106.7, 105.2, 94.5, 65.7, 56.1, 27.8, 25.7, 21.4, 17.6; HRMS (EI$^+$) calcd for C$_{23}$H$_{27}$NO$_5$S [M$^+$] 317.1627. found 317.1631.

Phosphonate F.

To benzylic alcohol D (333 mg, 0.775 mmol) in THF was added LiBr (540 mg, 6.20 mmol) and Et$_3$N (0.44 mL, 3.10 mmol) and the solution was cooled to 0° C. After 15 min MsCl (0.19 mL, 2.46 mmol) was added dropwise. The reaction was allowed to stir and slowly warm to rt. After 2 hours, when complete by TLC analysis, it was quenched by addition H$_2$O and extracted with Et$_2$O. The organic extracts were washed with brine, dried (MgSO$_4$), and filtered, and the filtrate was concentrated in vacuo. To the resulting residue was added P(OEt)$_3$ (3 mL) and the solution was heated at reflux overnight. The next day the solution was allowed to cool to rt and then poured into water and extracted with EtOAc. The organic extract was washed with brine, dried (MgSO$_4$), and filtered and the filtrate was concentrated in vacuo. Final purification by flash column chromatography (50 to 70% EtOAc in hexanes) afforded indole phosphonate F (384 mg, 90%): $^1$H NMR δ 7.82 (d, J=2.8 Hz, 1H), 7.69 (d, J=8.4 Hz, 2H), 7.21 (d, J=8.5 Hz, 2H), 6.87 (s, 1H), 6.43 (s, 1H), 5.40-5.35 (m, 1H), 5.25 (s, 2H), 4.07-3.94 (m, 4H), 3.64 (d, J=7.2 Hz, 2H), 3.48 (s, 3H), 3.26 (d, $J_{PH}$=21.3 Hz, 2H), 2.34 (s, 3H), 1.78 (s, 3H), 1.62 (s, 3H), 1.26 (t, J=7.1 Hz, 6H); $^{13}$C NMR δ 149.3 (d, $J_{CP}$=3.1 Hz) 144.6, 140.0 (d, $J_{CP}$=1.9 Hz), 138.5 (d, $J_{CP}$=3.1 Hz), 136.2, 134.7, 129.9 (2C), 128.1 (d, $J_{CP}$=9.3 Hz), 126.3 (2C), 119.5, 119.4 (d, $J_{CP}$=3.1 Hz), 109.9 (d, $J_{CP}$=7.4 Hz), 109.5 (d, $J_{CP}$=6.1 Hz), 105.2, 94.8, 62.2 (d, $J_{CP}$=6.9 Hz, 2C), 56.2, 34.2 (d, $J_{CP}$=137.7 Hz), 27.8, 25.6, 21.4, 17.7, 16.2 (d, $J_{CP}$=5.9 Hz, 2C); $^{31}$P NMR δ 27.3; HRMS (EI$^+$) calcd for $C_{27}H_{36}NO_7PS$ [M$^+$] 549.1950. found 549.1943.

Protected Analogue H.

To phosphonate F (74 mg, 0.14 mmol) and aldehyde E (30 mg, 0.10 mmol) in THF (2 mL) at 0° C. was added NaH (50 mg, 1.25 mmol, 60% dispersion oil) and 15-Crown-5 (3 drops). The reaction mixture was allowed to stir for 4 hours, then quenched by addition of NH$_4$Cl (sat) and extracted with EtOAc. The combined organic extracts were washed with brine, dried (MgSO$_4$), and filtered, and then concentrated in vacuo. Purification by flash column chromatography (50% EtOAc in hexanes) afforded a mixture of TV-tosyl indole G and unprotected indole H. To the mixed residue in 1:1 THF and 2-propanol (3 mL) at 0° C. was added NaH (120 mg, 3 mmol) and the reaction mixture allowed to warm to rt overnight. The next day the reaction mixture was quenched by addition of NH$_4$Cl (sat), diluted with H$_2$O, and extracted with EtOAc. The combined organic extracts were washed with water, brine, and dried (MgSO$_4$), filtered, and then the filtrate was concentrated in vacuo. Final purification by flash column chromatography (50% EtOAc in hexanes) afforded indole H (20 mg, 37% (2 steps)) as an oil: $^1$H NMR δ 7.92 (br s, 1H), 7.08 (m, 1H), 7.02 (d, J=16.1 Hz, 1H), 6.96 (m, 1H), 6.94 (d, J=16.1 Hz, 1H), 6.89 (m, 1H), 6.86 (m, 1H), 6.31 (m, 1H), 5.40 (m, 1H) 5.36 (s, 2H), 3.90 (s, 3H), 3.56 (s, 3H), 3.49-3.39 (m, 3H), 2.74-2.71 (m, 2H), 2.18-2.10 (m, 1H), 1.90-1.60 (m, 5H), 1.79 (s, 3H), 1.74 (s, 3H), 1.26 (s, 3H), 1.11 (s, 3H), 0.89 (s, 3H); $^{13}$CNMR δ 150.1, 148.9, 142.3, 138.3, 137.5, 134.6, 132.1, 129.5, 127.8, 126.4, 122.6, 120.1, 120.1, 119.9, 107.1, 106.9, 103.5, 102.3, 95.0, 78.1, 77.0, 56.1, 56.0, 46.8, 38.4, 37.7, 28.3, 27.4, 27.1, 25.7, 23.2, 19.9, 17.8, 14.3; HRMS (EI$^+$) calcd for $C_{34}H_{43}NO_5$ [M$^+$] 545.3141. found 545.3135.

Compound 6.

To analogue H (8 mg, 0.015 mmol) in MeOH (0.8 mL) in a foil-wrapped flask was added TsOH (25 mg, 0.13 mmol) and the reaction was allowed to stir. After 10 hours the reaction was quenched by addition of NaHCO$_3$ (sat) and extracted with EtOAc. The combined organic extracts were washed with brine, dried (MgSO$_4$), and filtered, and the filtrate was concentrated in vacuo. Final purification by radial chromatography (50% EtOAc in hexanes) afforded compound 6 (5 mg, 68%) as a light yellow oil: $^1$H NMR (CD$_3$OD) δ 6.99 (d, J=16.4 Hz, 1H), 6.95 (m, 2H), 6.90 (d, J=16.2 Hz, 1H), 6.82 (m, 1H), 6.63 (s, 1H), 6.17 (s, 1H), 5.46-5.41 (m, 1H), 3.85 (s, 3H), 3.44 (d, J=7.3 Hz, 2H), 3.37 (dd, J=10.8, 3.9 Hz, 1H), 2.76-2.73 (m, 2H), 2.07-2.02 (m, 1H), 1.85-1.60 (m, 4H), 1.79 (s, 3H), 1.75 (s, 3H), 1.23 (s, 3H), 1.11 (s, 3H), 0.88 (s, 3H); $^{13}$C NMR δ 150.5, 150.1, 143.2, 140.1, 139.4, 134.3, 132.9, 131.4, 129.3, 126.6, 124.0, 122.2, 121.4, 119.4, 108.0, 103.4, 102.0, 96.7, 78.7, 78.1, 56.4, ~49*, 39.5, 38.9, 29.0, 28.0, 27.9, 25.9, 24.1, 20.2, 17.8, 14.9; HRMS (EI$^+$) calcd for $C_{32}H_{39}NO_6$ [M$^+$] 502.2957. found 502.2956. *Obscured by solvent.

Example 3

Synthesis of Compound 7

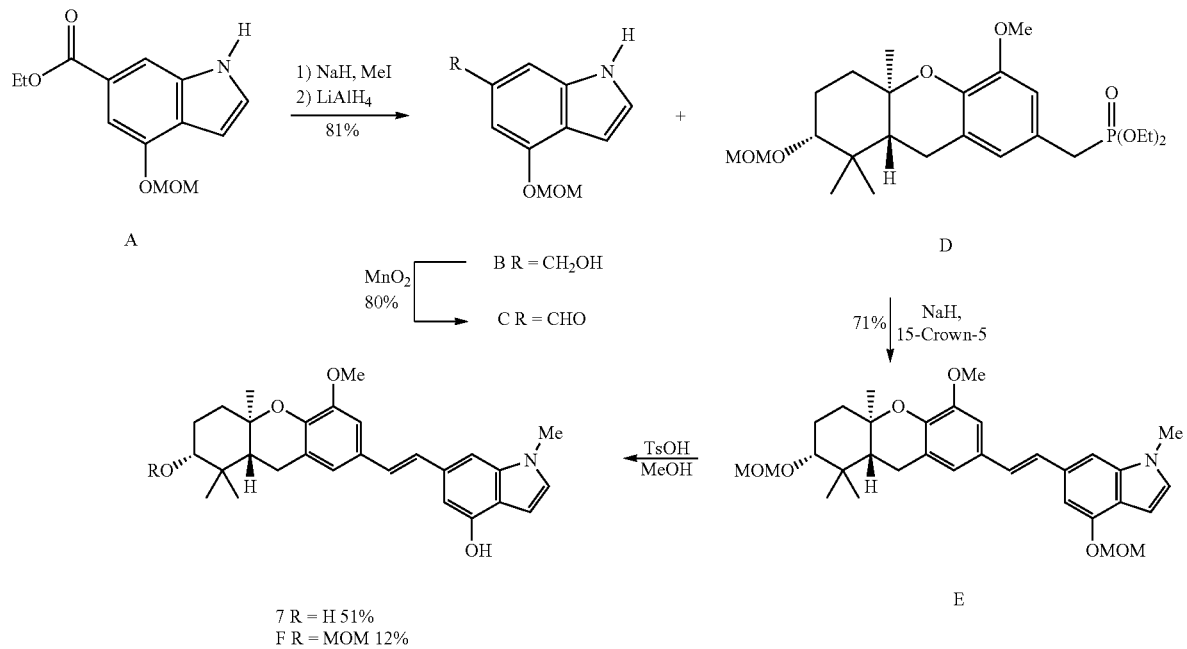

Alcohol B.

To indole A (202 mg, 0.81 mmol) in THF (10 mL) at 0° C. was added NaH (49 mg, 1.2 mmol, 60% dispersion in mineral oil) followed after 5 min by MeI (0.06 mL, 0.96 mmol), and the reaction mixture was allowed to stir for 2 hours. After LiAlH$_4$ (92 mg, 2.42 mmol) was added, the solution was allowed to stir for 1 h and then quenched with NH$_4$Cl (sat) and extracted with EtOAc. The combined organic extracts were washed with brine, dried (MgSO$_4$), and filtered, and the filtrate was concentrated in vacuo. Final purification by flash column chromatography (40% EtOAc in hexanes) afforded benzylic alcohol B (146 mg, 81%, 2 steps) as a light yellow solid: $^1$H NMR δ 6.96 (s, 1H), 6.91 (d, J=3.2 Hz, 1H), 6.70 (s, 1H), 6.53 (d, J=3.1 Hz, 1H), 5.27 (s, 2H), 4.69 (s, 2H), 3.65 (s, 3H), 3.48 (s, 3H), 2.68 (br s 1H); $^{13}$C NMR δ 150.3, 138.1, 135.7, 127.8, 118.9, 102.6, 102.2, 97.9, 94.4, 65.8, 56.0, 32.8; HRMS (EI$^+$) calcd for $C_{12}H_{15}NO_3$ [M$^+$] 221.1042. found 221.1042.

Aldehyde C.

To alcohol B (73 mg, 0.33 mmol) in CH$_2$Cl$_2$ (10 mL) at rt was added MnO$_2$ (430 mg, 4.9 mmol) and the resulting mixture was allowed to stir for 4 hours, then filtered through celite, and washed with EtOAc. The solvent was removed in vacuo to afford aldehyde C (58 mg, 80%) as a light yellow solid: $^1$H NMR δ 9.98 (s, 1H), 7.55 (s, 1H), 7.27 (s, 1H), 7.19 (d, J=2.9 Hz, 1H), 6.65 (d, J=2.8 Hz, 1H), 5.38, (s, 2H), 3.85 (s, 3H), 3.54 (s, 3H); $^{13}$C NMR δ 192.2, 150.7, 137.4, 131.8, 131.7, 124.8, 108.5, 102.0, 99.2, 94.5, 56.2, 33.2; HRMS (EI$^+$) calcd for $C_{12}H_{13}NO_3$ [M$^+$] 219.0895. found 219.0889.

Stilbene E.

To aldehyde C (11 mg, 0.05 mmol) and phosphonate D (27 mg, 0.06 mmol) in THF (1.5 mL) at rt was added NaH (40 mg, 1.0 mmol, 60% dispersion in oil). After the reaction mixture was allowed to stir for 6 hours, it was quenched by addition of NH$_4$Cl (sat) and then extracted with EtOAc. The combined organic layers were washed with brine, dried (MgSO$_4$), filtered, and the filtrate was concentrated in vacuo. Final purification by flash column chromatography (50% Et$_2$O in hexanes) afforded stilbene E (19 mg, 71%) as a light yellow oil: $^1$H NMR δ 7.11 (d, J=16.1 Hz, 1H), 7.10 (s, 1H), 7.01 (d, J=16.2 Hz, 1H), 7.00 (s, 1H), 6.98 (d, J=3.1 Hz, 1H), 6.92 (s, 1H), 6.89 (s, 1H), 6.56 (d, J=3.0 Hz, 1H), 5.39 (s, 2H), 4.78 (d, J=6.9 Hz, 1H), 4.66 (d, J=6.9 Hz, 1H), 3.92 (s, 3H), 3.72 (s, 3H), 3.57 (s, 3H), 3.42 (s, 3H), 3.29 (dd, J=11.5, 4.0, Hz, 1H), 2.74-2.71 (m, 2H), 2.17-2.12 (m, 1H), 1.87-1.57 (m, 4H), 1.25 (s, 3H), 1.10 (s, 3H), 0.92 (s, 3H); $^{13}$C NMR δ 150.7, 148.9, 142.3, 138.4, 132.7, 129.3, 128.2, 127.7, 126.8, 122.6, 120.2, 119.5, 106.7, 102.3, 101.5, 98.4, 96.1, 94.8, 76.9, 56.1, 55.7, 55.6, 47.0, 38.2, 37.6, 33.0, 30.3, 29.7, 25.3, 23.1, 19.8, 15.1; HRMS (EI$^+$) calcd for $C_{32}H_{41}NO_6$ [M$^+$] 535.2934. found 535.2919.

Compound 7.

To stilbene E (19 mg 0.035 mmol) in a 1:1 mixture of THF and MeOH (2 mL) was added TsOH (30 mg, 0.16 mmol) and the resulting solution was allowed to stir at rt overnight. It was then quenched by addition of NaHCO$_3$ (sat) and extracted with EtOAc. The combined organic layers were washed with brine, dried (MgSO$_4$), and filtered and then concentrated in vacuo. Final purification by flash column chromatography (40% EtOAc in hexanes) afforded Compound 7 (8 mg, 51%) as a light yellow oil along with MOM protected analogue F (2 mg, 12%). For analogue 7: $^1$H NMR δ 7.05 (d, J=16.1 Hz, 1H), 7.00 (s, 1H), 6.98 (d, J=3.1 Hz, 1H), 6.97 (d, J=16.5 Hz, 1H), 6.91 (s, 1H), 6.87 (s, 1H), 6.77 (s, 1H), 6.50 (d, J=3.1 Hz, 1H), 5.24 (br s, 1H), 3.91 (s, 3H), 3.79 (s, 3H), 3.44 (dd, J=11.6, 3.8 Hz, 1H), 2.75-2.72 (m, 2H), 2.17-2.11 (m 1H), 1.90-1.55 (m 5H), 1.25 (s, 3H), 1.11 (s, 3H), 0.89 (s, 3H); $^{13}$C NMR δ 148.9, 148.9, 142.3, 138.8, 132.9, 129.3, 128.2, 127.5, 127.0, 122.6, 120.3, 117.8, 106.6, 101.6, 101.5, 97.4, 78.0, 56.0, 46.7, 38.4, 37.6, 33.1, 29.7, 28.2, 27.3, 19.8, 14.3; HRMS (EI$^+$) calcd for $C_{28}H_{33}NO_4$ [M$^+$] 447.2410. found 447.2422.

Example 4

Synthesis of Compound 8

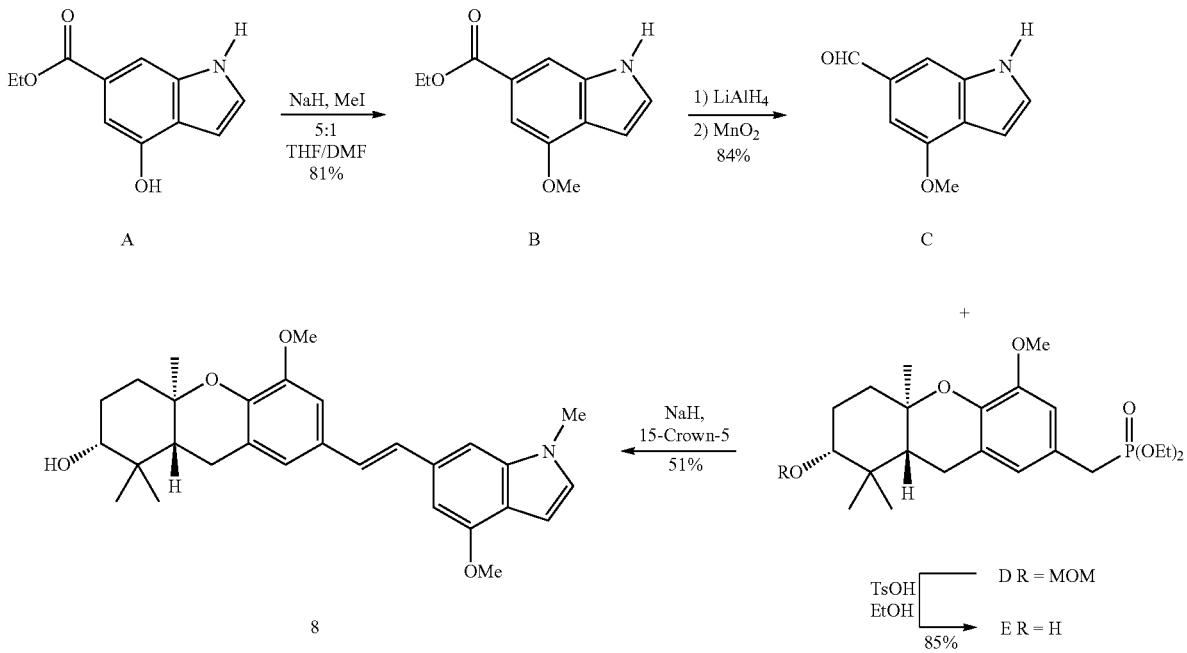

Synthesis of Dimethyl Indole B.

To indole A (500 mg, 2.43 mmol) in a mixture of THF and DMF (5:1) at 0° C. was added NaH (224 mg, 5.6 mmol, as a 60% dispersion in oil), followed after 20 min by MeI (0.34 mL, 5.35 mmol). The reaction was allowed to stir for 3 hours, then quenched by addition of NH$_4$Cl (sat), and finally extracted with EtOAc. The combined organic extracts were washed with brine, dried (MgSO$_4$), filtered and the filtrate was concentrated in vacuo. Final purification by flash column chromatography (20% EtOAc in hexanes) afforded indole B (460 mg, 81%) as a white solid with $^1$H and $^{13}$C NMR spectra identical to those of material previously synthesized via an alternate route.

Aldehyde C.

To indole B (54 mg, 0.24 mmol) in THF (5 mL) at 0° C. was added LiAlH$_4$ (28 mg, 0.73 mmol), and the reaction was allowed to warm to rt over 50 min. It was then quenched by addition by NH$_4$Cl (sat) and extracted with EtOAc. The combined organic layers were washed with brine, dried (MgSO$_4$), and filtered, and the solvent was removed in vacuo. The resulting residue was then dissolved in CH$_2$Cl$_2$ (10 mL) and MnO$_2$ (315 mg, 3.62 mmol) was added. After the reaction mixture was allowed to stir for 4 hours, it was filtered through celite and the solvent was removed in vacuo to afford aldehyde C (38 mg, 84%, for 2 steps) as a light yellow solid: $^1$H NMR δ 9.98 (s, 1H), 7.48 (s, 1H), 7.17 (d, J=2.9 Hz, 1H), 7.05 (s, 1H), 6.64 (d, J=2.7 Hz, 1H), 4.00 (s, 3H), 3.85 (s, 3H); $^{13}$C NMR δ 192.2, 153.5, 137.0, 132.0, 131.4, 124.2, 109.3, 99.4, 97.1, 55.4 33.2; HRMS (EI$^+$) calcd for C$_{11}$H$_{11}$NO$_2$ [M$^+$] 189.0790. found 189.0787.

Phosphonate E.

To phosphonate D$^{45}$ (81 mg, 0.17 mmol) in EtOH (3 mL) was added TsOH (80 mg, 0.42 mmol) and the reaction flask was wrapped in foil. The solution was allowed to stir for 2 days, then quenched by addition of NaHCO$_3$ (sat), and extracted with EtOAc. The combined organic layers were washed with brine, dried (MgSO$_4$), and filtered, and then concentrated in vacuo. Final purification by flash column chromatography (3% EtOH in Et$_2$O) afforded phosphonate E (62 mg, 85%) as a colorless oil whose $^1$H and $^{13}$C NMR spectra were in agreement with those of material prepared by another route.

Compound 8.

To phosphonate E (31 mg, 0.073 mmol) and aldehyde C (12 mg, 0.063 mmol) in THF (1 mL) was added NaH (40 mg, 1.0 mmol, 60% dispersion in oil) and 15-Crown-5 (1 drop). The solution was allowed to stir overnight, then quenched by addition of NH$_4$Cl (sat) and finally extracted with EtOAc. The combined organic extracts were washed with brine, dried (MgSO$_4$), and filtered, and the filtrate was concentrated in vacuo. Final purification by flash column chromatography (45% EtOAc in hexanes) afforded Compound 8 (15 mg, 51%) as a yellow oil: $^1$H NMR δ 7.11 (d, J=16.1 Hz, 1H), 7.04-6.99 (m, 2H), 6.96 (d, J=3.2 Hz, 1H), 6.93 (d, J=1.6 Hz, 1H), 6.90 (d, J=1.5 Hz, 1H), 6.75 (s, 1H), 6.55 (d, J=2.9 Hz, 1H), 4.02 (s, 3H), 3.92 (s, 3H), 3.79 (s, 3H), 3.44 (dd, J=11.7, 4.0 Hz, 1H), 2.75-2.72 (m, 2H), 2.17-2.12 (m 1H), 1.90-1.60 (m, 5H), 1.27 (s, 3H), 1.11 (s, 3H), 0.90 (s, 3H); $^{13}$C NMR δ 153.3, 148.9, 142.3, 138.3, 132.6, 129.4, 128.0, 127.9, 126.6, 122.6, 120.2, 118.8, 106.7, 101.8, 98.5, 97.2, 78.0, 77.0, 56.0, 55.3, 46.7, 38.4, 37.6, 33.1, 28.3, 27.4, 23.2, 19.8, 14.3; HRMS (EI$^+$) calcd for C$_{29}$H$_{35}$NO$_4$ [M$^+$] 461.2566; found 461.2569.

Example 5

Synthesis of Compound 11

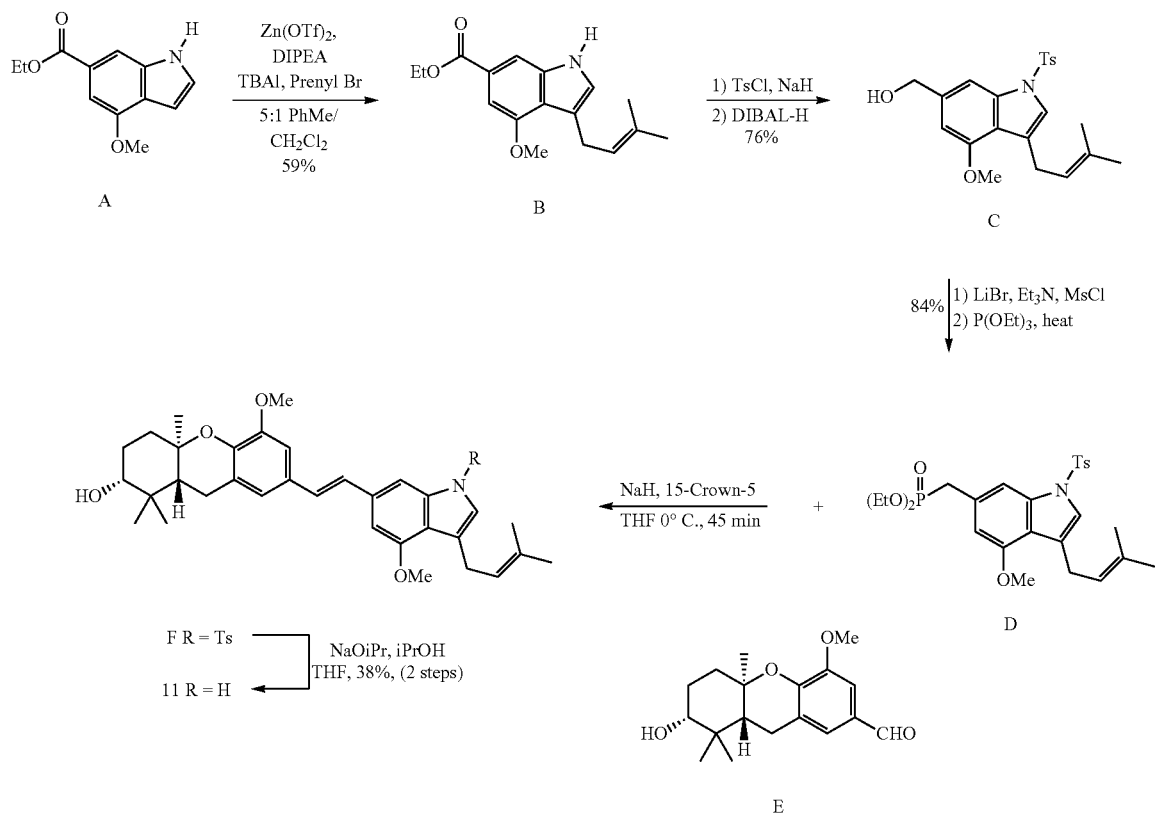

Prenylated Indole B.

To indole A (388 mg, 1.77 mmol), TBAI (360 mg, 0.98 mmol), and Zn(OTf)$_2$ (436 mg, 1.2 mmol) in a 5:1 mixture of toluene and CH$_2$Cl$_2$ (12 mL) at rt was added DIPEA (0.38 mL, 2.2 mmol) and the reaction mixture was allowed to stir for 10 min. Prenyl bromide (126 mg, 0.88 mmol) was added dropwise. After 2 hours the reaction mixture was quenched by addition of NH₄Cl (sat) and extracted with EtOAc. The combined organic extracts were washed with H₂O, dried (MgSO₄), and filtered, and the filtrate was concentrated in vacuo. Final purification by flash column chromatography (10% to 15% EtOAc in hexanes) afforded prenylated indole B (209 mg, 59%) along with recovered indole A as expected[94] (149 mg): ¹H NMR δ 8.31 (brs, 1H), 7.74 (d, J=1.0 Hz, 1H), 7.15 (d, J=0.5 Hz, 1H), 6.93 (m, 1H), 5.47-5.42 (m, 1H), 4.39 (q, J=7.1 Hz, 1H), 3.95 (s, 3H), 3.63 (d, J=7.2 Hz, 2H), 1.75 (s, 3H), 1.72 (s, 3H), 1.40 (t, J=7.2 Hz, 3H); ¹³C NMR δ 167.8, 154.4, 137.1, 131.5, 124.6, 123.7, 123.2, 120.8, 117.1, 107.4, 99.8, 60.7, 55.3, 25.7, 25.4, 17.7, 14.4; HRMS (EI⁺) calcd for $C_{17}H_{21}NO_3$ [M⁺] 287.1521. found 287.1523.

Alcohol C.

To a solution of indole B (18 mg, 0.06 mmol) in THF (3 mL) at rt was added NaH (5 mg, 0.13 mmol, 60% dispersion oil) and the reaction mixture was allowed to stir for 10 min. After TsCl (15 mg, 0.08 mmol) was added, the solution was stirred for 2 hours and then DIBAL-H (0.05 mL, 0.44 mmol) was added dropwise. After an additional 30 min, the reaction was quenched by addition of NH₄Cl (sat), poured into EtOAc, acidified with 1M HCl, and extracted with EtOAc. The combined organic extracts were washed with NaHCO₃ (sat), and brine, dried (MgSO₄), and filtered, and the filtrate was concentrated in vacuo. Final purification by flash column chromatography (35% EtOAc in hexanes) afforded the benzylic alcohol C (19 mg, 76%): ¹H NMR δ 7.70 (d, J=8.1 Hz, 2H), 7.53 (s, 1H), 7.15 (d, J=8.3 Hz, 2H), 7.10 (s, 1H), 6.64 (s, 1H), 5.39-5.35 (m, 1H), 4.72 (s, 2H), 3.82 (s, 3H), 3.49 (d, J=7.1 Hz, 2H), 2.29 (s, 3H), 1.76 (s, 3H), 1.68 (s, 3H); ¹³C NMR δ 154.7, 144.6, 139.0, 136.9, 135.2, 132.9, 129.7 (2C), 126.6, (2C), 123.1, 121.8, 121.5, 119.8, 104.9, 102.9, 65.7, 55.2, 25.7, 25.6, 21.4, 17.7; HRMS (EI⁺) calcd for $C_{22}H_{25}NO_4S$ [M⁺] 399.1504. found 399.1508.

Phosphonate D.

To alcohol C (102 mg, 0.25 mmol) in THF (5 mL) at 0° C. was added LiBr (133 mg, 1.53 mmol) and Et₃N (0.11 mL, 0.79 mmol). The solution was stirred for 5 min, MsCl (0.05 mL, 0.65 mmol) was added dropwise, and the reaction was allowed to warm to rt. After 2 hours it was quenched by addition of NH₄Cl (sat), extracted with Et₂O, dried (MgSO₄), and filtered, and the filtrate was concentrated in vacuo. To the resulting residue was added P(OEt)₃ (2 mL) and the solution was heated to 130° C. and allowed to stir overnight. The next day the solution was allowed to cool to rt and the solvent was removed in vacuo. Final purification by flash column chromatography (2% EtOH in Et₂O) afforded indole phosphonate D (111 mg, 84%) as a colorless oil: ¹H NMR δ 7.72 (d, J=8.4 Hz, 2H), 7.50 (d, $J_{HP}$=2.3 Hz, 1H), 7.19 (d, J=8.2 Hz, 2H), 7.07 (d, J=1.1 Hz, 1H), 6.62 (s, 1H), 5.40-5.34 (m, 1H), 4.06-3.92 (m, 4H), 3.84 (s, 3H), 3.48 (d, J=7.1 Hz, 2H), 3.23 (d, $J_{HP}$=21.5 Hz, 2H), 2.32 (s, 3H), 1.76 (s, 3H), 1.67 (s, 3H), 1.24 (t, J=7.1 Hz, 6H); ¹³C NMR δ 154.3 (d, $J_{CP}$=2.9 Hz), 144.4, 136.9 ($J_{CP}$=2.9 Hz), 135.2, 132.9, 129.7 (2C), 129.1 ($J_{CP}$=9.8 Hz), 126.7 (2C), 123.1 (d, $J_{CP}$=1.7 Hz), 121.7, 121.3 (d, $J_{CP}$=1.6 Hz), 119.3 (d, $J_{CP}$=3.2 Hz), 107.8 (d, $J_{CP}$=7.8 Hz), 105.8 (d, $J_{CP}$=5.6 Hz), 62.0 (d, $J_{CP}$=2.9 Hz, 2C), 55.2, 34.2 (d, $J_{CP}$=138.2 Hz), 25.7, 25.6, 21.4, 17.7, 16.3 (d, $J_{CP}$=6.0 Hz, 2C); ³¹P NMR δ 26.2; HRMS (EI⁺) calcd for $C_{26}H_{34}NO_6PS$ [M⁺] 519.1844. found 519.1843.

Compound 11.

To phosphonate D (45 mg, 0.089 mmol) and aldehyde E (21 mg, 0.069 mmol) in THF (1 mL) at 0° C. was added NaH (40 mg, 1.0 mmol, 60% dispersion oil) and 15-Crown-5 (2 drops). The reaction mixture was allowed to stir for 45 min, then quenched by addition of NH₄Cl (sat), and extracted with EtOAc. The combined organic extracts were washed with brine, dried (MgSO₄), and filtered, and then the filtrate was concentrated in vacuo. Purification by flash column chromatography (20% to 50% EtOAc in hexanes) afforded a mixture of protected and unprotected indole (26 mg). This mixture was treated with NaOi-Pr in THF (3 mL), generated in situ from NaH (160 mg, 4 mol, 60% dispersion oil) and i-PrOH, and the reaction mixture was allowed to stir overnight. The next day the reaction mixture was quenched by addition of H₂O and extracted with EtOAc. The combined organic extracts were washed with water and brine, dried (MgSO₄), and filtered, and the filtrate was concentrated in vacuo. Final purification by flash column chromatography (45% EtOAc in hexanes) afforded indole 11 (13.5 mg, 38% (2 steps)) as a light yellow oil: ¹H NMR δ 7.90 (br s, 1H), 7.03 (d, J=16.0 Hz, 1H), 7.01 (s, 1H), 6.96 (d, J=16.2 Hz, 1H), 6.91 (m, 1H), 6.88 (m, 1H), 6.79-6.78 (m, 1H), 6.68 (s, 1H) 5.49-5.44 (m, 1H), 3.97 (s, 3H), 3.90 (s, 3H), 3.61 (d, J=7.2 Hz, 2H), 3.46-3.41 (m, 1H), 2.75-2.72 (m, 2H), 2.17-2.10 (m, 1H), 1.91-1.59 (m, 5H), 1.75 (s, 3H), 1.73 (s, 3H), 1.26 (s, 3H), 1.11 (s, 3H), 0.89 (s, 3H); ¹³C NMR δ 155.0, 148.9, 142.3, 138.3, 132.9, 131.2, 129.5, 127.9, 126.5, 124.0, 122.6, 120.5, 120.2, 117.2, 117.0, 106.9, 103.3, 97.4, 78.1, 77.0, 56.0. 55.1, 46.8, 38.3, 37.7, 28.3, 27.3, 25.8, 25.6, 23.3, 19.8, 17.7, 14.3; HRMS (EI⁺) calcd for $C_{33}H_{41}NO_4$ [M⁺] 515.3036; found 515.3040.

Example 6

Synthesis of Compound 9

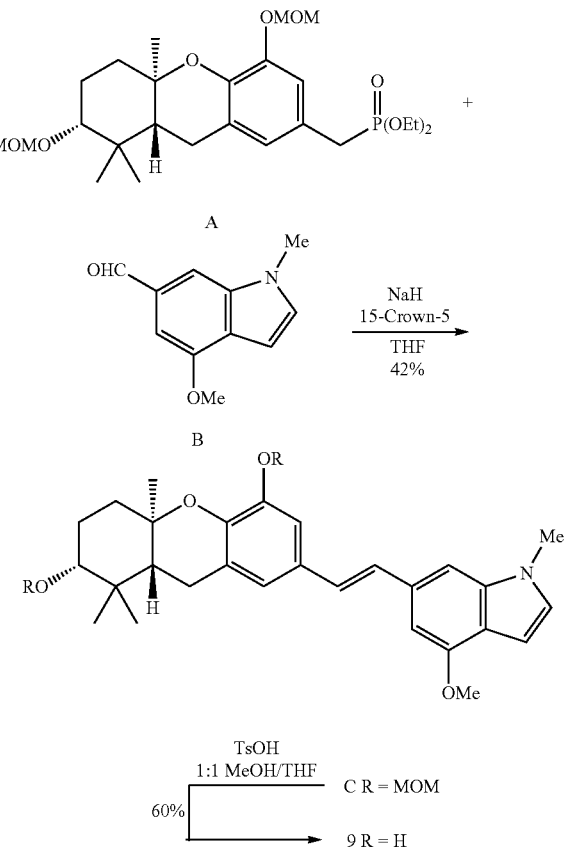

Compound C.

To aldehyde B (15 mg, 0.08 mmol) and phosphonate A (48 mg, 0.10 mmol) in THF (3 mL) at 0° C. was added NaH (40 mg, 1.0 mmol, 60% dispersion oil) and 15-Crown-5 (2 drops) and the reaction mixture was allowed to warm to rt. The following day the reaction mixture was quenched by addition of NH$_4$Cl (sat) and extracted with EtOAc. The combined organic extracts were washed with brine, dried (MgSO$_4$), and filtered, and the filtrate was concentrated in vacuo. Final purification by flash column chromatography (20% EtOAc in hexanes) afforded analogue C (18 mg, 42%) as a light yellow oil: $^1$H NMR δ 7.17 (d, J=1.7 Hz, 1H), 7.08 (d, J=16.8 Hz, 1H), 7.03 (s, 1H), 6.99 (d, J=16.4 Hz, 1H), 6.98 (d, J=1.4 Hz, 1H), 6.94 (d, J=3.1 Hz, 1H), 6.73 (s, 1H), 6.54 (d, J=2.9 Hz, A1H), 5.25 (d, J=6.7 Hz, 1H), 5.21 (d, J=6.5 Hz, 1H), 4.78 (d, J=6.9 Hz, 1H), 4.65 (d, J=6.8 Hz, 1H), 4.01 (s, 3H), 3.78 (s, 3H), 3.55 (s, 3H), 3.41 (s, 3H), 3.29 (dd, J=11.5, 3.9 Hz, 1H), 2.75-2.72 (m, 2H), 2.13-1.97 (m, 2H), 1.80-1.57 (m, 3H), 1.26 (s, 3H), 1.10 (s, 3H), 0.91 (s, 3H); $^{13}$C NMR δ 153.3, 146.2, 143.6, 138.3, 132.7, 129.6, 128.2, 127.8, 126.4, 123.2, 121.7, 118.9, 113.4, 101.8, 98.5, 97.3, 96.2, 95.9, 84.0, 76.9, 56.2, 55.6, 55.3, 47.1, 38.3, 37.7, 33.0, 27.3, 25.3, 23.2, 19.9, 15.1; HRMS (EI$^+$) calcd for C$_{32}$H$_{41}$NO$_6$ [M$^+$] 535.2934; found 535.2933.

Compound 9.

To di-MOM protected analogue C (18 mg, 0.034 mmol) in 1:1 MeOH:THF (0.8 mL) protected from ambient light was added TsOH (50 mg, excess) and the resulting solution was allowed to stir overnight. The reaction mixture was quenched by addition of NH$_4$Cl (sat) and extracted with EtOAc. The combined organic layers were washed with brine, dried (MgSO$_4$), and filtered and the filtrate was concentrated in vacuo. Final purification by flash column chromatography (50% EtOAc in hexanes) afforded Compound 9 (9 mg, 60%) as a light green oil: $^1$H NMR δ 7.08 (d, J=16.2 Hz, 1H), 7.02 (s, 1H), 7.00-6.95 (m, 2H), 6.94 (d, J=3.0 Hz, 1H), 6.82 (d, J=1.5 Hz, 1H), 6.73 (s, 1H), 6.54 (d, J=2.6 Hz, 1H), 5.46 (br s, 1 OH), 4.01 (s, 3H), 3.78 (s, 3H), 3.45 (dd, J=11.3, 4.0 Hz, 1H), 2.74-2.70 (m, 2H), 2.06-2.01 (m, 1H), 1.91-1.60 (m, 4H), 1.55 (brs, 1 OH), 1.26 (s, 3H), 1.12 (s, 3H), 0.90 (s, 3H); $^{13}$C NMR δ 153.3, 145.2, 139.7, 138.4, 132.7, 130.3, 128.3, 127.9, 126.5, 122.0, 119.2, 118.9, 119.4, 101.8, 98.5, 97.3, 77.9, 77.9, 55.3, 47.2, 38.5, 37.7, 33.0, 28.2, 27.3, 22.7, 20.2, 14.3; HRMS (EI$^+$) calcd for C$_{28}$H$_{33}$NO$_4$ [M$^+$] 447.2410. found 447.2404.

Example 7

Synthesis of Compound 12

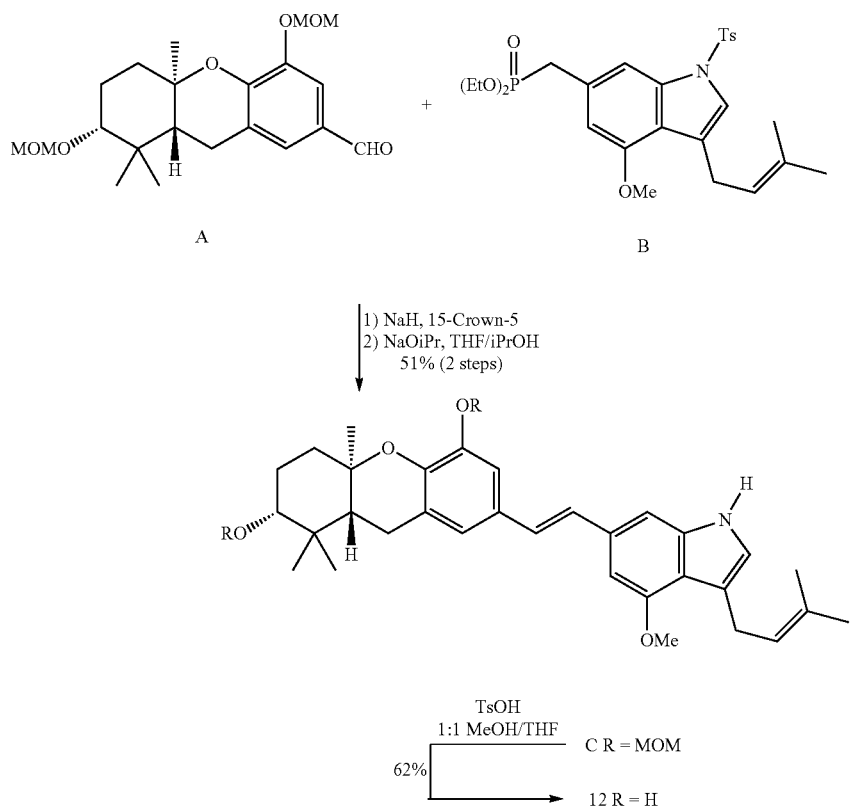

Compound C.

To phosphonate B (45 mg, 0.089 mmol) and aldehyde A (25.7 mg, 0.068 mmol) in THF (3 mL) at 0° C. was added NaH (50 mg, 1.25 mmol, 60% dispersion oil) and 15-Crown-5 (2 drops). The reaction was allowed to warm to rt and then allowed to stir for 4 hours. To the reaction mixture was added 2-propanol (3 mL) and NaH (40 mg, 1.0 mmol, 60% dispersion oil) and the solution was allowed to stir. After 20 hours the reaction was quenched by addition of NaHCO$_3$ and extracted with EtOAc. The combined organic extracts were washed with brine, dried (MgSO$_4$), and filtered, and the filtrate was concentrated in vacuo. Final purification by flash column chromatography (40% EtOAc in hexanes) afforded indole C (20 mg, 51% for 2 steps) as a light yellow oil: $^1$H NMR δ 7.89 (br s, 1H), 7.15 (d, J=1.4 Hz, 1H), 7.00 (s, 1H), 6.99 (s, 1H), 6.97 (m, 2H), 6.78 (d, J=1.1 Hz, 1H), 6.68 (s, 1H), 5.49-5.44 (m, 1H), 5.25 (d, J=6.6 Hz, 1H), 5.20 (d, J=6.6 Hz, 1H), 4.78 (d, J=6.9 Hz, 1H), 4.65 (d, J=6.9 Hz, 1H), 3.97 (s, 3H), 3.61 (d, J=7.2 Hz, 2H), 3.55 (s, 3H), 3.41 (s, 3H), 3.29 (dd, J=11.6, 3.9 Hz, 1H), 2.75-2.71 (m, 2H), 2.13-1.94 (m, 2H), 1.75-1.55 (m, 3H), 1.75 (s, 3H), 1.73 (s, 3H), 1.26 (s, 3H), 1.10 (s, 3H), 0.91 (s, 3H); $^{13}$C NMR δ 155.0, 146.2, 143.6, 138.3, 132.9, 131.2, 129.6, 128.0, 126.3, 124.7, 123.3, 121.7, 120.5, 117.2, 117.0, 113.4, 103.4, 97.4, 96.2, 95.9, 84.0, 76.9, 56.2, 55.6, 55.1, 47.1, 38.3, 37.7, 27.4, 25.8, 25.6, 25.3, 23.2, 19.9, 17.7, 14.3; HRMS (EI$^+$) calcd for $C_{36}H_{47}NO_6$ [M$^+$] 589.3426. found 589.3416.

Compound 12.

To protected analogue C (12.2 mg, 0.021 mmol) was added 1:1 THF/MeOH (2 mL) and TsOH (35 mg, 0.184 mmol) and the reaction mixture was allowed to stir overnight. The next day the reaction mixture was quenched by addition of NH$_4$Cl and extracted with EtOAc. The combined organic extracts were washed with brine, dried (MgSO$_4$), and filtered, and the filtrate was concentrated in vacuo. Final purification by flash column chromatography (25% to 50% EtOAc in hexanes) afforded Compound 12 (6.4 mg, 62%) as an oil: $^1$H NMR δ 7.89 (brs, 1H), 7.01 (d, J=16.1 Hz, 1H), 7.00 (s, 1H), 6.97 (d, J=1.9 Hz, 1H), 6.93 (d, J=16.2 Hz, 1H), 6.80-6.78 (m, 2H), 6.67 (s, 1H), 5.49-5.44 (m, 2H), 3.97 (s, 3H), 3.61 (d, J=7.2 Hz, 2H), 3.45 (dd, J=11.2, 4.0 Hz, 1H), 2.78-2.63 (m, 2H), 2.06-2.00 (m, 1H), 1.93-1.58 (m, 5H), 1.75 (s, 3H), 1.73 (s, 3H), 1.25 (s, 3H), 1.12 (s, 3H), 0.89 (s, 3H); $^{13}$C NMR δ 155.0, 145.2, 139.7, 138.3, 132.9, 131.2, 130.3, 128.2, 126.4, 124.1, 122.0, 120.5, 119.2, 117.2, 117.1, 109.4, 103.4, 97.4, 77.9, 77.8, 55.1, 47.2, 38.5, 37.7, 28.2, 27.3, 25.8, 25.6, 22.7, 20.2, 17.7, 14.3; HRMS (EI$^+$) calcd for $C_{32}H_{39}NO_4$ [M$^+$] 501.2879. found 501.2881.

Example 8

Synthesis of Compound 13

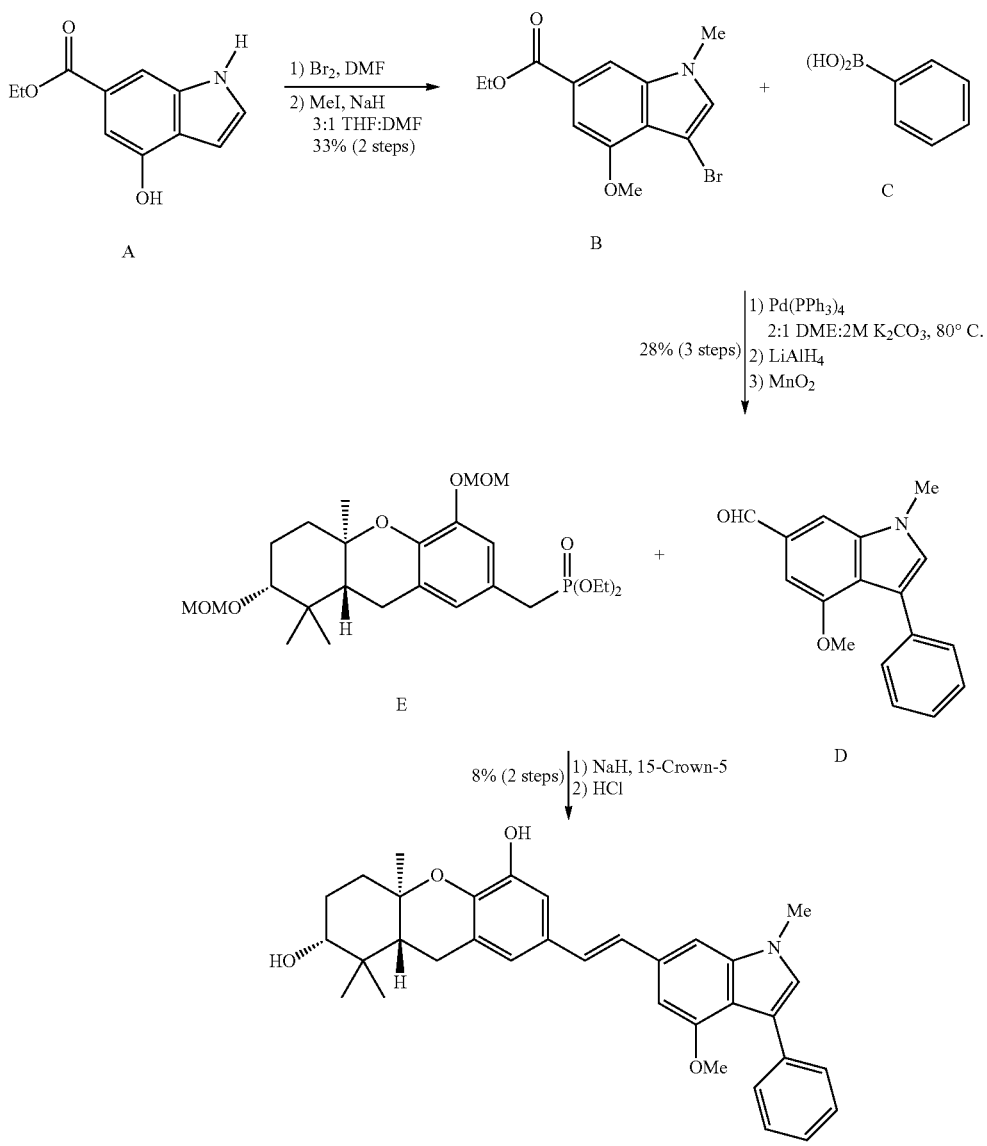

Compound B.

To phenol A (2.731 g, 13.3 mmol) in DMF (70 mL) in a foil wrapped flask was added $Br_2$ (0.68 mL, 13.3 mmol) and the reaction mixture was allowed to stir overnight. The following day the reaction mixture was quenched by addition of $NaHCO_3$ (sat) and extracted with EtOAc. The combined organic extracts were washed with water, brine, dried (MgSO/t), filtered and the solvent was removed in vacuo. The residue was partially purified by flash column chromatography (20% to 50% EtOAc in hexanes) to afford a solid which was used in the next step without further purification. The resulting solid was then dissolved in a 3:1 mixture of THF:DMF (60 mL) and cooled to 0° C. Next MeI was added (2.0 mL, 31.7 mmol) followed by NaH (1.27 g, 31.7 mmol) and the reaction mixture was allowed to stir for a couple of hours. The reaction was quenched by addition of $NH_4Cl$ (sat) and then extracted with EtOAc. The combined organic extracts were washed with brine, dried ($MgSO_4$), filtered and the solvent was removed in vacuo. Final purification by column chromatography (0% to 30% EtOAc in hexanes afforded bromide B (1.364 g, 33%) as a solid: $^1$H NMR δ 7.71 (m, 1H), 7.19 (m, 1H), 7.08 (s, 1H), 4.41 (q, J=7.1 Hz, 2H), 3.99 (s, 3H), 3.78 (s, 3H), 1.43 (t, J=7.1 Hz, 3H); $^{13}$C 167.2, 153.4, 137.2, 130.2, 125.5, 119.8, 105.7, 100.7, 86.9, 61.0, 55.7, 33.4, 14.4.

Compound D.

To bromide B (130 mg, 0.42 mmol) in 2:1 DME: 2N $K_2CO_3$ (6 mL) was added boronic acid C (100 mg, 0.82 mmol) and $Pd(PPh_3)_4$ (70 mg, 0.061 mmol) and the reaction mixture was heated to 80° C. for several hours. After the reaction was judged complete by TLC analysis, it was allowed to cool to rt then water was added and subsequently extracted with EtOAc. The combined organics extracts were washed with brine, dried ($MgSO_4$), filtered and the solvent was removed in vacuo. Partial purification by flash column chromatography (0% to 10% EtOAc in hexanes) afforded a solid. The resulting solid was dissolved in THF (10 mL) and $LiAlH_4$ (60 mg, 1.58 mmol) was added. The reaction mixture was allowed to stir for 1 hour then quenched by addition of $NH_4Cl$ (sat) and then extracted with EtOAc. The combined organics extracts were washed with brine, dried ($MgSO_4$), filtered and the solvent was removed in vacuo. Purification by flash column chromatography (0% to 30% EtOAc in hexanes) afforded material that was used directly in the next step. The resulting residue was dissolved in $CH_2Cl_2$ (10 mL) and $MnO_2$ (0.4 g, 4.60 mmol) was added and then the reaction mixture was allowed to stir overnight. The reaction mixture was filtered through celite and the pad was washed several times with EtOAc. The resulting filtrate was concentrated in afforded aldehyde D (31 mg, 28% 3 steps) as a white solid: $^1$H NMR δ 10.01 (s 1H), 7.59-7.57 (m, 2H), 7.51 (s, 1H), 7.41-7.38 (m, 2H), 7.32-7.27 (m, 1H), 7.21 (s, 1H), 7.09 (s, 1H), 3.88 (m, 6H); $^{13}$C 192.2, 154.8, 138.0, 134.9, 132.0, 130.7, 129.6 (2C), 127.6 (2C), 126.0, 120.5, 118.4, 109.0, 97.9, 55.2, 33.3.

Compound 13.

To aldehyde D (30 mg, 0.11 mmol) and phosphonate E (68 mg, 0.14 mmol) in THF (3 mL) was added NaH (40 mg, 1.0 mmol) as a 60% dispersion oil followed by a couple of drops of 15-crown-5. The reaction mixture was allowed to stir for 2 hours and then quenched by addition of $NaHCO_3$ (sat) and extracted with EtOAc. The combined organic extracts were washed with brine, dried ($MgSO_4$), filtered and the solvent was removed in vacuo. The residue was then dissolved in 1:1 THF:MeOH (4 mL) and cone. HCl (0.15 mL, 1.8 mmol) was added and the reaction mixture was allowed to stir overnight and then was quenched by addition of $NH_4Cl$ (sat) and extracted with EtOAc. The combined organics extracts were dried ($MgSO_4$), filtered and the solvent was removed in vacuo. Final purification by flash column chromatography (0% to 50% EtOAc in hexanes) afforded analogue 13 (5 mg, 8%) as a solid: $^1$H NMR δ 7.63-7.60 (m, 2H), 7.39-7.34 (m, 2H), 7.27-7.25 (m, 1H) 7.09 (d, J=16.3 Hz, 1H), 7.04 (s, 1H), 7.07-6.99 (m, 2H), 7.00 (d, J=16.1 Hz, 1H), 6.84 (s, 1H), 6.77 (s, 1H), 5.48 (br s, 1H), 3.88 (s, 3H), 3.82 (s, 3H), 3.49-3.43 (m, 1H), 2.79-2.63 (m, 2H), 2.07-1.57 (m, 5H), 1.57 (br s, 1H), 1.26 (s, 3H), 1.13 (s, 3H), 0.90 (s, 3H).

Example 9

Synthesis of Compound 14

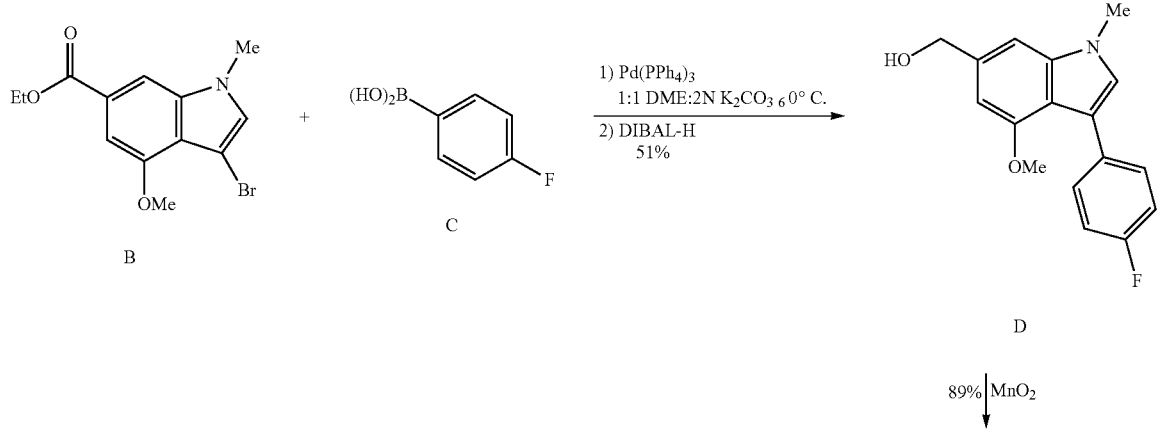

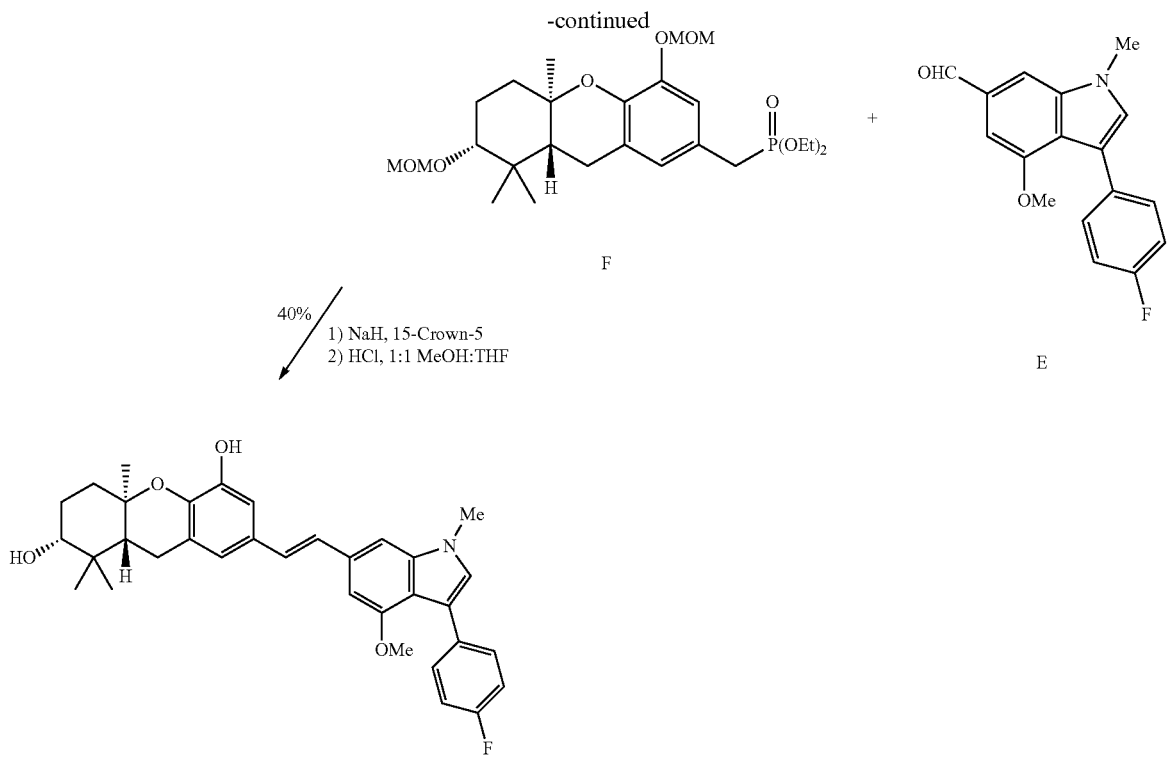

Compound D.

To bromide B (338 mg, 1.08 mmol) and boronic acid C (227 mg, 1.62 mmol) in a 1:1 DME:2N $K_2CO_3$ (20 mL) was added $Pd(PPh_3)_4$ (88 mg, 0.076 mmol) and then the reaction mixture was heated to 60° C. for 90 minutes and then allowed to cool to rt. The reaction mixture was quenched by addition of water and then extracted with EtOAc. The combined organic extracts were dried ($MgSO_4$), filtered and the solvent was removed in vacuo. The residue was then dissolved in THF (10 mL) then DIBAL-H (1.0 mL, 5.6 mmol) was added and the reaction mixture was allowed to stir for one hour and then quenched by addition of $NH_4Cl$ (sat). To the resulting solution was added EtOAc and 1N NaOH to break up the solids and then extracted with EtOAc. The combined organic extracts were washed with water, brine, dried ($MgSO_4$), filtered and the solvent was removed in vacuo. Final purification by flash column chromatography (0% to 30% EtOAc in hexanes) afforded alcohol D (158 mg, 51%) as an light yellow solid: $^1$H NMR δ 7.56-7.51 (m, 2H), 7.08-7.02 (m, 2H), 6.99 (s, 1H), 6.96 (s, 3H), 6.58 (s, 1H), 4.81 (s, 2H), 3.83 (s, 3H), 3.79 (s, 3H), 1.71 (br s, 1H); $^{13}$C δ 161.4 (d, $J_{CF}$=243.7 Hz), 154.5, 138.8, 136.1, 131.8 (d, $J_{CF}$=3.0 Hz), 130.8 (d, $J_{CF}$=7.6 Hz, 2C), 126.7, 116.3, 115.3, 114.3 (d, $J_{CF}$=21.1 Hz, 2C), 101.4, 99.5, 66.3, 55.1, 33.1; $^{19}$F δ-118.2.

Compound E.

To alcohol D (143 mg, 0.5 mmol) in $CH_2Cl_2$ (10 mL) was added $MnO_2$ (700 mg, 7.52 mmol) and the reaction mixture was allowed to stir overnight and then the reaction was filtered through celite and the pad was then washed several times with EtOAc. The resulting filtrate was concentrated in vacuo to afford aldehyde E (127 mg, 89%) as a light yellow solid: $^1$H NMR δ 10.12 (s, 1H), 7.53-7.48 (m, 3H), 7.16 (s, 1H), 7.08-7.03 (m, 3H), 3.87 (m, 6H); $^{13}$C δ 192.1, 161.6 (d, $J_{CF}$=244.7 Hz), 154.5, 137.9, 132.0, 131.0 (d, $J_{CF}$=7.8 Hz, 2C), 130.9 (d, $J_{CF}$=3.3 Hz), 130.5, 120.4, 117.3, 114.4 (d, $J_{CF}$=21.3 Hz, 2C), 109.0, 97.8, 56.2, 33.2; $^{19}$F δ-117.2.

Compound 14.

To aldehyde E (18 mg, 0.064 mmol) and phosphonate F (43 mg, 0.083 mmol) in THF (2 mL) was added NaH (20 mg, 0.5 mmol) as a 60% dispersion oil followed by a couple of drops of 15-crown-5. The reaction mixture was allowed to stir for until judged complete by TLC analysis and then quenched by addition of $NaHCO_3$ (sat) and then extracted with EtOAc. The combined organic extracts were washed with brine, dried ($MgSO_4$), filtered and the solvent was removed in vacuo. Purification by flash column chromatography (0% to 25% EtOAc in hexanes) afforded the coupled product that was then dissolved in 1:1 THF:MeOH (2 mL) and conc. HCl (0.1 mL, 1.2 mmol) was added. The following day the reaction mixture was quenched by addition of $NH_4Cl$ (sat) and extracted with EtOAc. The combined organic extracts were dried ($MgSO_4$), filtered and the solvent was removed in vacuo. Final purification by flash column chromatography (0% to 45% EtOAc in hexanes) afforded Compound 14 (13.8 mg, 40%) as a solid: $^1$H NMR δ 7.57-7.52 (m, 2H), 7.08 (d, J=16.2 Hz, 1H), 7.07-7.00 (m, 4H), 6.99 (d, J=16.1 Hz, 1H), 6.94 (s, 1H), 6.83 (s, 1H), 6.76 (s, 1H), 5.47 (br s, 1H), 3.88 (s, 3H), 3.80 (s, 3H), 3.47-3.42 (m, 1H), 2.75-2.27 (m, 2H), 2.07-2.01 (m, 1H), 1.91-1.60 (m, 4H), 1.54 (br s, 1H), 1.26 (s, 3H), 1.12 (s, 3H), 0.90 (s, 3H); $^{13}$C δ 161.5 (d, $J_{CF}$=243.4 Hz), 154.5, 145.3, 139.2, 139.2, 130.0, 131.8, 130.8 (d, $J_{CF}$=7.8 Hz, 2C), 130.2, 127.9, 127.0, 120.0 119.3, 116.7, 115.6, 114.4 (d, $J_{CF}$=21.1 Hz, 2C), 109.5, 98.2, 77.9, 55.2, 47.2, 38.5, 37.7, 33.0, 28.2, 27.4, 22.7, 20.2, 14.3; $^{19}$F δ-118.2.

Example 10

Synthesis of Compound 15

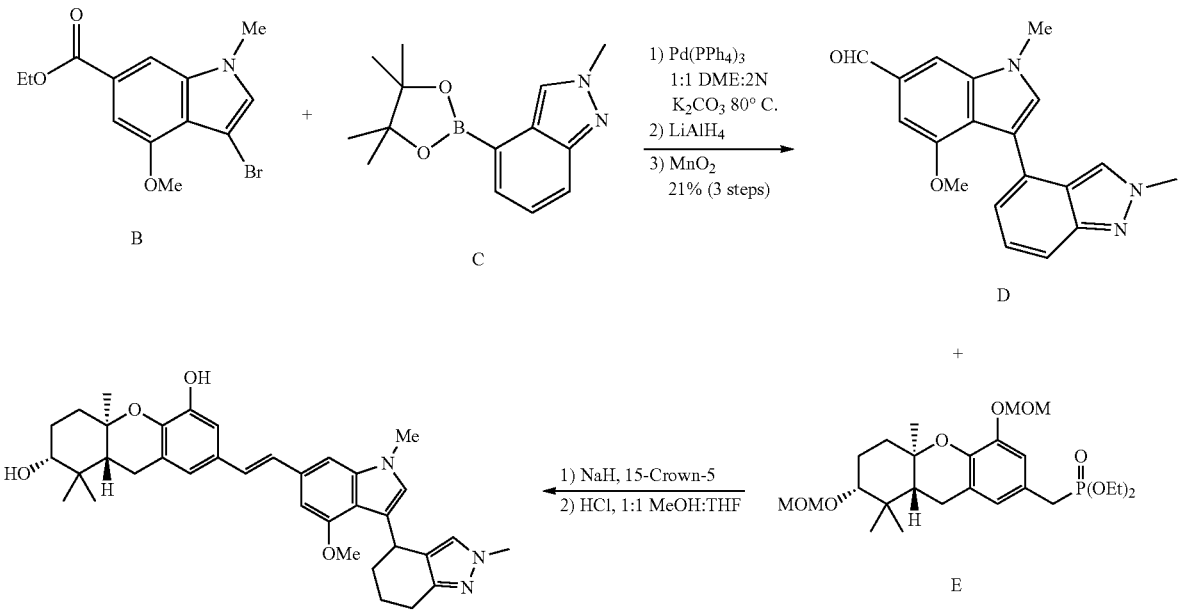

Compound D.

To bromide B (154 mg, 0.49 mmol) and boronic ester C (116 mg, 0.45 mmol) in 1:1 DME:2N K$_2$CO$_3$ (10 mL) was allowed to stir for 10 minutes then Pd(PPh$_3$)$_4$ (40 mg, 0.034 mmol) was added. The reaction mixture was heated to 80° C. and was allowed to stir until judged complete by TLC analysis. The reaction mixture was then allowed to cool to rt and quenched by the addition of water and then extracted with EtOAc. The combined organic extracts were washed with brine, dried, (MgSO$_4$), filtered and the solvent was removed in vacuo. Purification by flash column chromatography (40% to 90% EtOAc in hexanes) afforded the coupled product that was used directly in the next step. The resulting residue was dissolved in THF (10 mL) and then LiAlH$_4$ (100 mg, 2.63 mmol) was added and the reaction mixture was allowed to stir for one hour and then quenched by addition of NH$_4$Cl (sat). The reaction mixture was diluted with water and extracted with EtOAc. The combined organic extracts were washed with brine, dried (MgSO$_4$) filtered and then the solvent was removed in vacuo. The resulting residue was dissolved in CH$_2$Cl$_2$ (10 mL) and MnO$_2$ (1.0 g, 11.5 mmol) was added and the reaction mixture was allowed to stir overnight. The following day the reaction mixture was filtered through celite and the pad was washed several times with EtOAc and then the filtrate was concentrated in vacuo. Final purification by flash column chromatography (60% to 100% EtOAc in hexanes) afforded aldehyde D (30 mg, 21%) as a light yellow solid: $^1$H NMR δ 10.02 (s, 1H), 7.77 (s, 1H), 7.64 (d, 8.7 Hz, 1H), 7.54 (s, 1H), 7.36-7.30 (m, 1H), 7.30 (s, 1H), 7.14 (d, J=6.9 Hz, 1H), 7.09 (s, 1H), 4.17 (s, 1H), 3.91 (s, 3H), 3.73 (s, 3H); $^{13}$C δ 192.0, 154.7, 149.1, 138.0, 132.3, 130.9, 127.5, 125.9, 124.4, 123.5, 122.5, 121.3, 116.0, 115.2, 108.8, 98.2, 55.2, 40.2, 33.3.

Compound 15.

To aldehyde D (30 mg, 0.094 mmol) and phosphonate E (60 mg, 0.12 mmol) in THF (1 mL) was added NaH (30 mg, 0.75 mmol) as a 60% dispersion oil followed by a couple of drops of 15-crown-5. The reaction mixture was then allowed to stir overnight and then quenched by addition of NaHCO$_3$ (sat) and then extracted with EtOAc. The combined organic extracts were washed with brine, dried (MgSO$_4$), filtered and the solvent was removed in vacuo. Purification by flash column chromatography (0% to 5% EtOH in CH$_2$Cl$_2$) afforded the coupled product that was then dissolved in 1:1 THF:MeOH (2 mL) and conc. HCl (0.1 mL, 1.2 mmol) was added and the reaction mixture was allowed to stir overnight in a foil wrapped flask. The reaction mixture was quenched by addition of NaHCO$_3$ (sat) and extracted with EtOAc. The combined organic extracts were washed with brine, dried (MgSO$_4$), filtered and the solvent was removed in vacuo. Final purification by flash column chromatography (0% to 5% EtOH in CH$_2$Cl$_2$) afforded analogue 15 (7.4 mg, 14%) as a solid: $^1$H NMR δ 7.85 (s, 1H), 7.62 (d, J=8.6 Hz, 1H), 7.36-7.31 (m, 1H), 7.18 (d, J=6.9 Hz, 1H), 7.13-7.07 (m, 2H), 7.10 (s, 1H), 7.01 (s, 1H), 7.01 (d, J=15.9 Hz, 1H), 6.84 (s, 1H), 6.77 (s, 1H), 5.50 (br s, 1H), 4.12 (s, 3H), 3.85 (s, 3H), 3.73 (s, 3H), 3.48-3.43 (m, 1H), 2.75-2.71 (m, 1H), 2.07-2.02 (m, 1H), 1.92-1.57 (m, 5H), 1.26 (s, 3H), 1.13 (s, 3H), 0.90 (s, 3H); $^{13}$C δ 154.4, 145.3, 139.8, 139.2, 137.0, 133.2, 130.1, 128.5, 127.9, 127.6, 127.0, 126.1, 124.9, 123.5, 122.1, 122.1 119.3, 116.4, 115.3, 114.6, 109.5, 101.8, 98.5, 77.9, 55.1, 47.2, 40.2 38.5, 37.7, 33.1 28.2, 27.4, 22.7, 20.2, 14.3.

Example 11

The following illustrate representative pharmaceutical dosage forms, containing a compound of formula (I) ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

We claim:

1. A compound of formula (I):

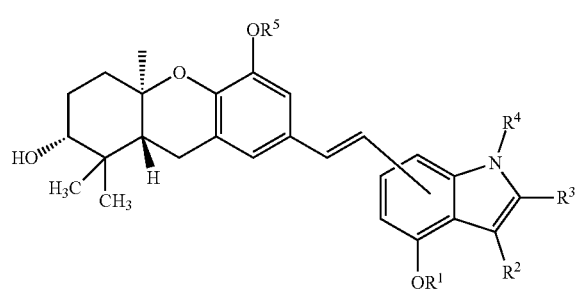

wherein:

$R^1$ is H or $(C_1$-$C_6)$alkyl;

$R^2$ is H, $(C_1$-$C_{15})$alkyl, $(C_2$-$C_{15})$alkenyl, aryl, or heteroaryl, wherein any aryl or heteroaryl is optionally substituted with one or more groups independently selected from halo, nitro, trifluoromethyl, trifluoromethoxy, nitro, cyano, $(C_1$-$C_6)$alkyl, $(C_3$-$C_6)$cycloalkyl, $(C_3$-$C_6)$cycloalkyl$(C_1$-$C_6)$alkyl, $(C_1$-$C_6)$alkoxy, $(C_1$-$C_6)$alkanoyl, $(C_1$-$C_6)$alkoxycarbonyl, and $(C_2$-$C_6)$alkanoyloxy;

$R^3$ is H, $(C_1$-$C_{15})$alkyl, or $(C_2$-$C_{15})$alkenyl;

$R^4$ is H or $(C_1$-$C_6)$alkyl; and $R^5$ is H or $(C_1$-$C_6)$alkyl;

or a salt thereof;

provided $R^2$ is not $(C_2$-$C_5)$alkenyl; and provided the compound of formula (I) is not:

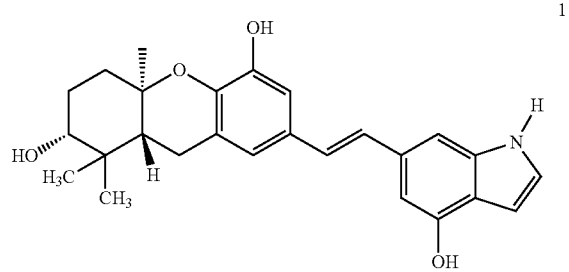

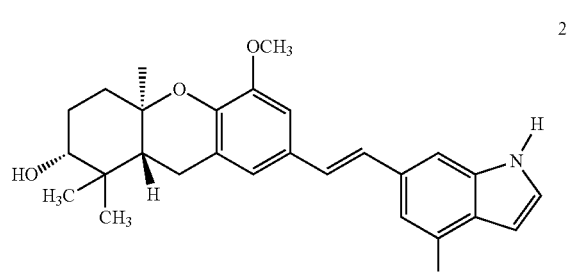

-continued

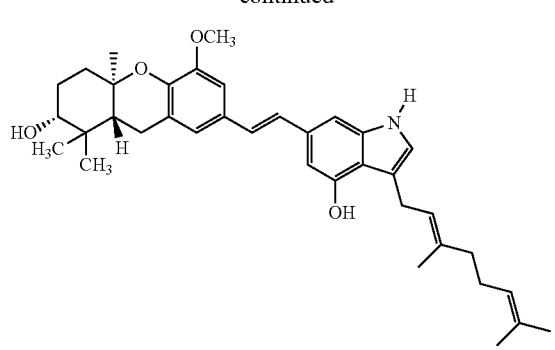
3

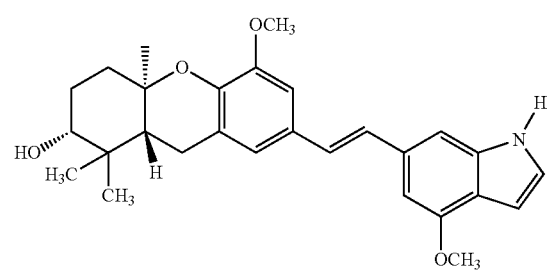
4

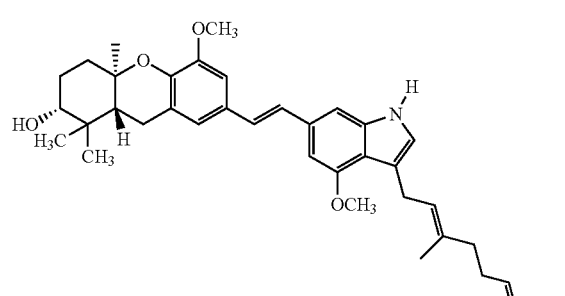
5

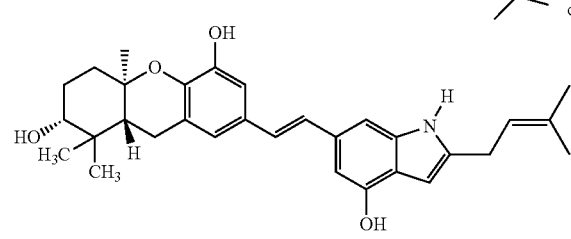
6

2. The compound of claim 1 which is a compound of formula (Ia):

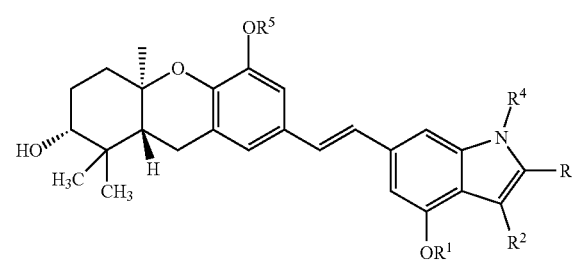
(Ia)

or a salt thereof.

3. The compound of claim 1 wherein $R^2$ is $(C_1-C_{15})$alkyl.

4. The compound of claim 1 herein $R^2$ is phenyl, 4-fluorophenyl, or 2-methyl-2(H)-indazol-4-yl.

5. The compound of claim 1 wherein $R^1$ is methyl; $R^2$ is phenyl, 4-fluorophenyl, or 2-methyl-2(H)-indazol-4-yl; $R^3$ is H; and $R^4$ is methyl.

6. The compound of claim 1 wherein $R^3$ is $(C_1-C_{15})$alkyl or $(C_2-C_{15})$alkenyl.

7. The compound of claim 1 wherein $R^4$ is $(C_1-C_6)$alkyl.

8. The compound of claim 1 wherein $R^4$ is methyl.

9. A compound selected from:

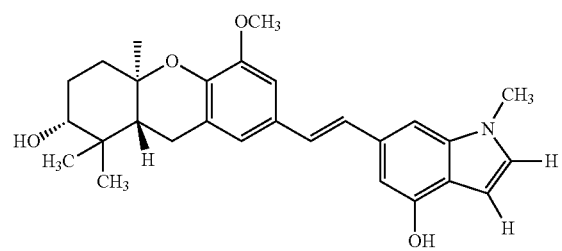
7

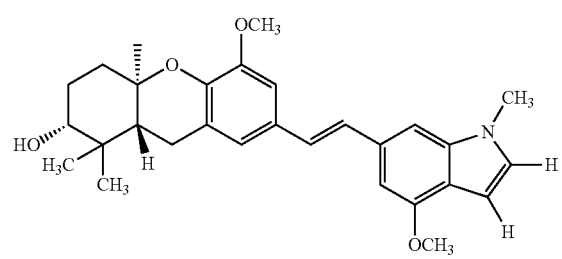
8

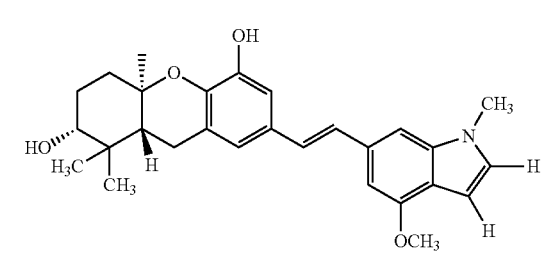
9

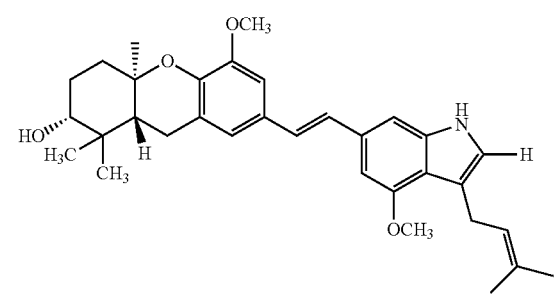
12 or a salt thereof.

10. A compound selected from:

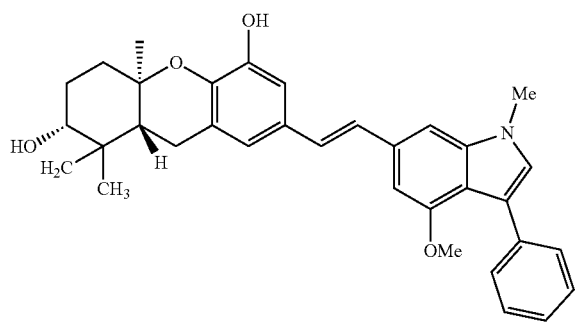

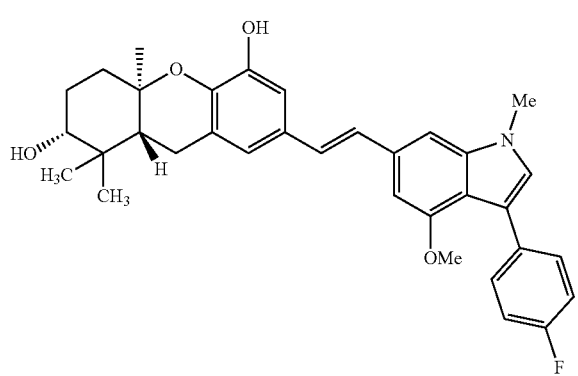

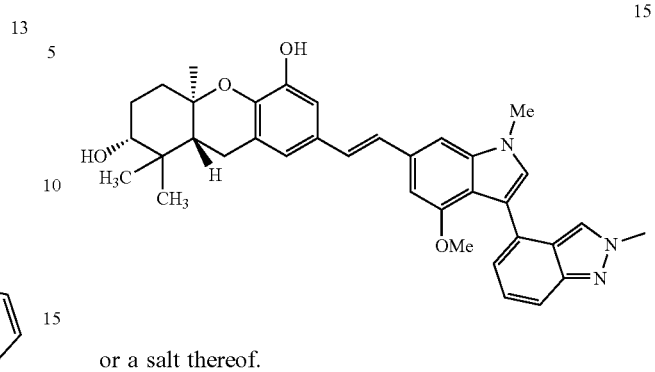

or a salt thereof.

11. A pharmaceutical composition comprising a compound of formula (I) as described in claim 1 or a pharmaceutically acceptable salt thereof, and a pharmaceutically acceptable carrier.

12. A method for treating cancer comprising administering a therapeutically effective amount of a compound of formula (I) as described in claim 1 or a pharmaceutically acceptable salt thereof to an animal, wherein the cancer is lung, glioma, leukemia, colon, melanoma, ovarian, renal, prostate, and breast cancer.

13. A method for treating lung cancer comprising administering a therapeutically effective amount of a compound of formula (I) as described in claim 1 or a pharmaceutically acceptable salt thereof to an animal.

14. A method for treating cancer comprising administering a therapeutically effective amount of a compound of formula (I) as described in claim 1 or a pharmaceutically acceptable salt thereof to an animal, wherein the cancer is brain cancer.

\* \* \* \* \*